United States Patent
Harris et al.

(10) Patent No.: US 8,266,949 B2
(45) Date of Patent: Sep. 18, 2012

(54) APPARATUS AND METHOD FOR MEASURING RHEOLOGICAL PROPERTIES OF A FLUID CONTAINING PARTICULATE

(75) Inventors: Phillip C. Harris, Duncan, OK (US); Harold G. Walters, Duncan, OK (US)

(73) Assignee: Halliburton Energy Services Inc., Duncan, OK (US)

( * ) Notice: Subject to any disclaimer, the term of this patent is extended or adjusted under 35 U.S.C. 154(b) by 483 days.

(21) Appl. No.: 12/561,695

(22) Filed: Sep. 17, 2009

(65) Prior Publication Data
US 2011/0061451 A1 Mar. 17, 2011

(51) Int. Cl.
*G01N 11/14* (2006.01)
(52) U.S. Cl. ............... 73/54.32; 73/54.28; 73/54.31
(58) Field of Classification Search ........... 73/54.31, 73/54.32
See application file for complete search history.

(56) References Cited

U.S. PATENT DOCUMENTS

| | | | |
|---|---|---|---|
| 5,799,734 | A | 9/1998 | Norman et al. |
| 6,782,735 | B2 | 8/2004 | Walters et al. |
| 7,392,842 | B2 | 7/2008 | Morgan et al. |

FOREIGN PATENT DOCUMENTS

DE 1184119 12/1964

OTHER PUBLICATIONS

J.F. Steffe, Rheological Methods in Food Process Engineering (second edition), Freeman Press, East Lansing, MI.

K. L. Mackey, R. G. Morgan and J. F. Steffe, "Effects of Shear-Thinning Behavior on Mixer Viscometry Techniques," Michigan Agricultural Experiment Station Journal Article No. 12280, Apr. 1, 1987.
Phillip C. Harris, Harold Walters, Haliburton Energy Services, Inc., "Real-Time Control of Low-Polymer Fracturing Fluids," SPE Annual Technical Conference and Exhibition, Oct. 1-4, 2000, Dallas, Texas.
P.C. Harris, R.G. Morgan and S.J. Heath, Haliburton Energy Services, Inc., "Measurement of Proppant Transport of Frac Fluids," SPE Annual Technical Conference and Exhibition, Oct. 9-12, 2005, Dallas, Texas.
Phillip C. Harris, Harold G. Walters and Jason Bryant, Haliburton Energy Services, Inc., "Prediction of Proppant Transport from Rheological Data," SPE Annual Technical Conference and Exhibition, Sep. 21-24, 2008, Denver, Colorado, USA.
Phil Harris, Haliburton, "Viscometer expands frac-fluid evaluation," Hart's E&P, Mar. 19, 2008.

*Primary Examiner* — Hezron E Williams
*Assistant Examiner* — Paul West
(74) *Attorney, Agent, or Firm* — Robert A. Kent; McDermott Will & Emery LLP

(57) ABSTRACT

An apparatus and a method for testing a viscosified fluid containing particulate indicate when the particulate is in suspension within the fluid and when it is not. The apparatus and method stir the fluid and particulate mixture for a time during which the viscosity of the fluid changes such that during a first period of the stirring time substantially all the particulate remains suspended in the fluid and during a second period of the stirring time substantially all the particulate settles out of suspension in the fluid. A signal is generated during the first and second periods such that the signal has a characteristic that changes from the first period to the second period to indicate the change in particle carrying ability of the fluid. Other characteristics, including crosslinking time, can also be determined. A test chamber includes projections extending from the inner surface of a cup receiving the fluid and from an axial support extending into the fluid in the cup.

46 Claims, 9 Drawing Sheets

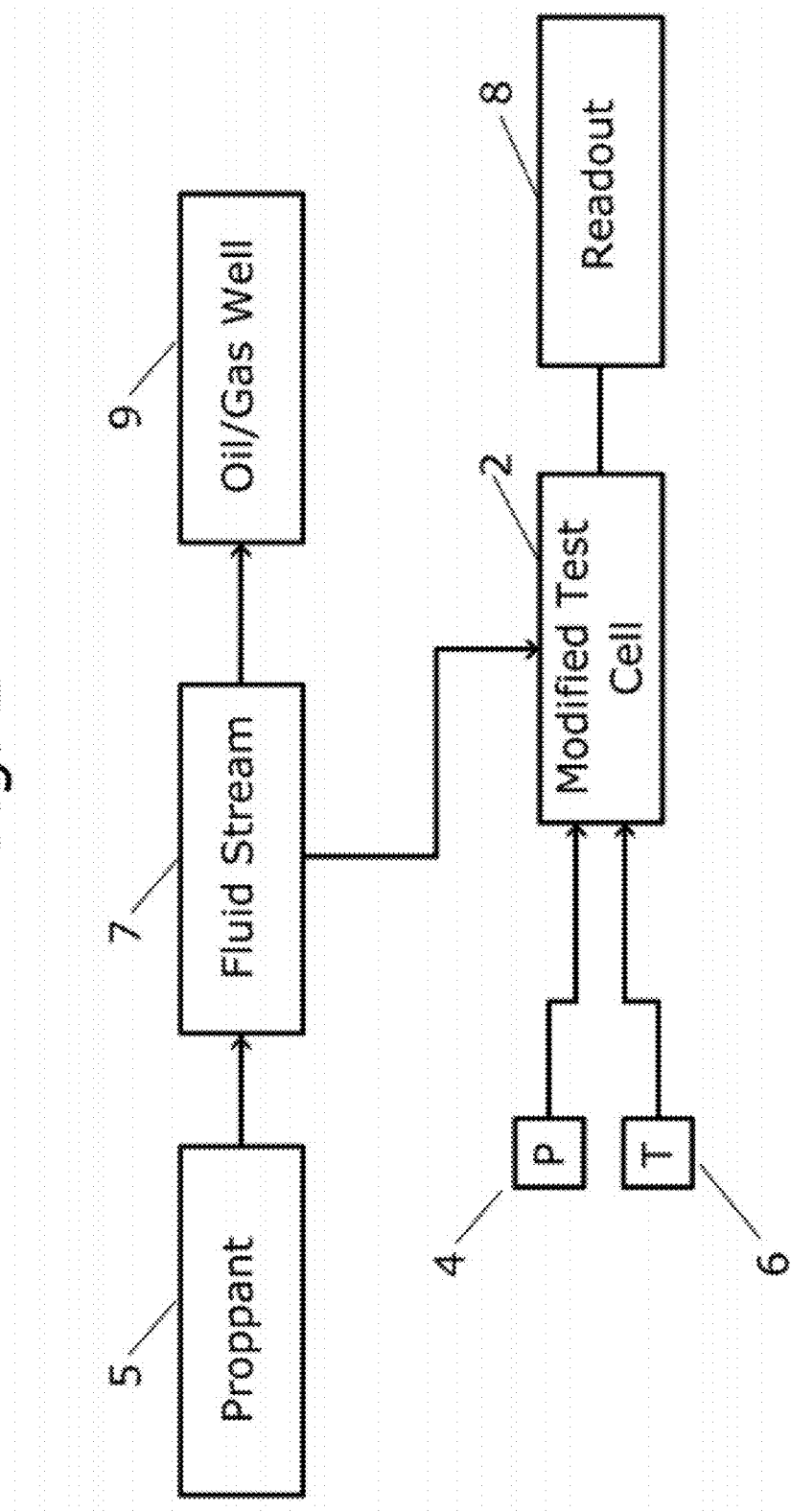

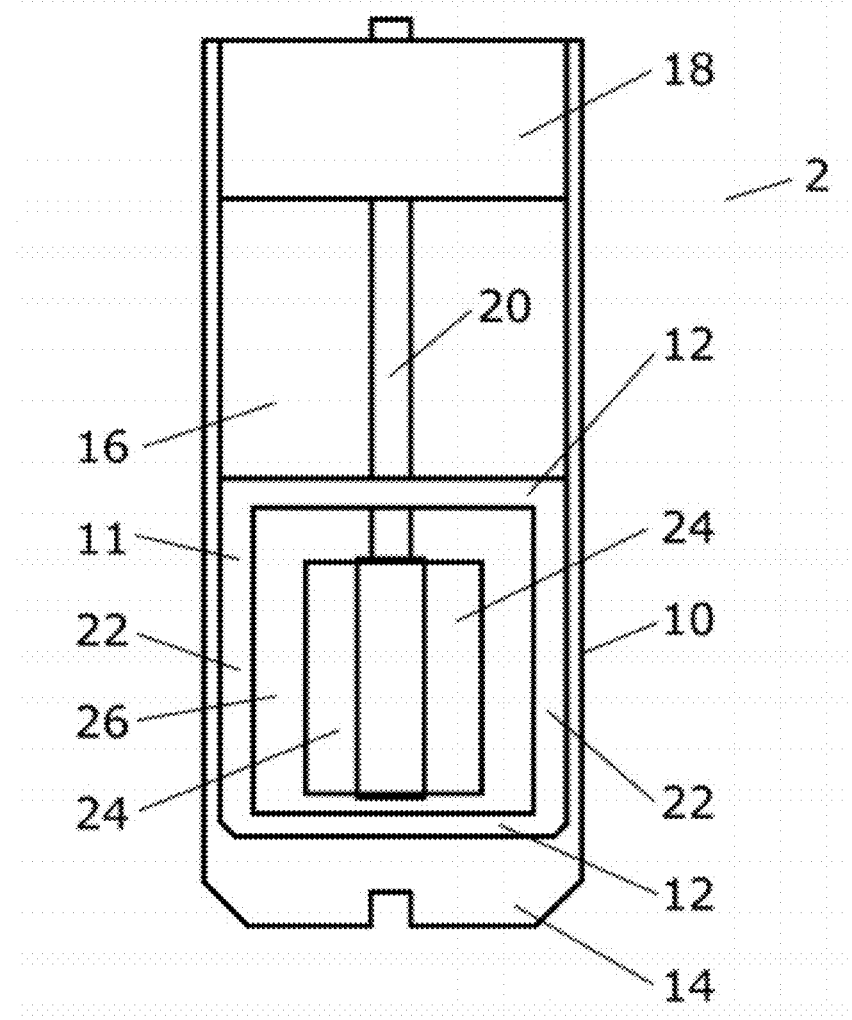

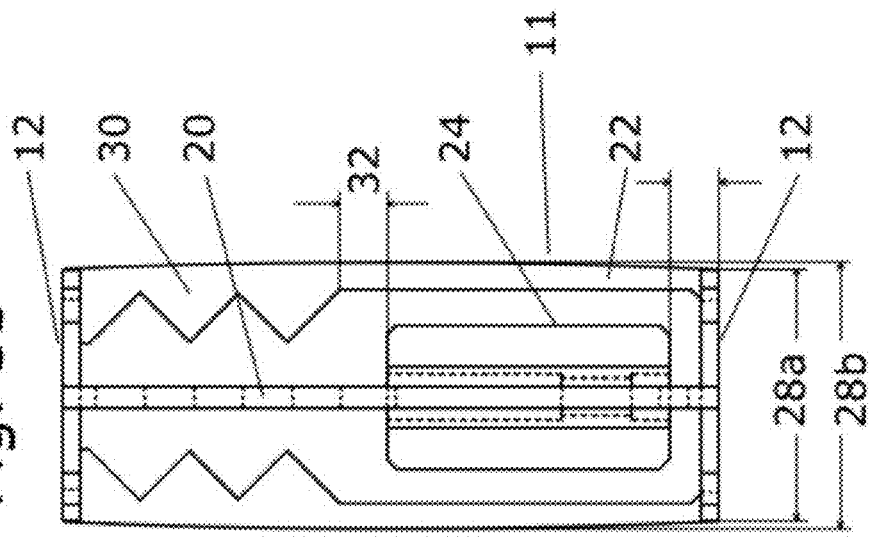
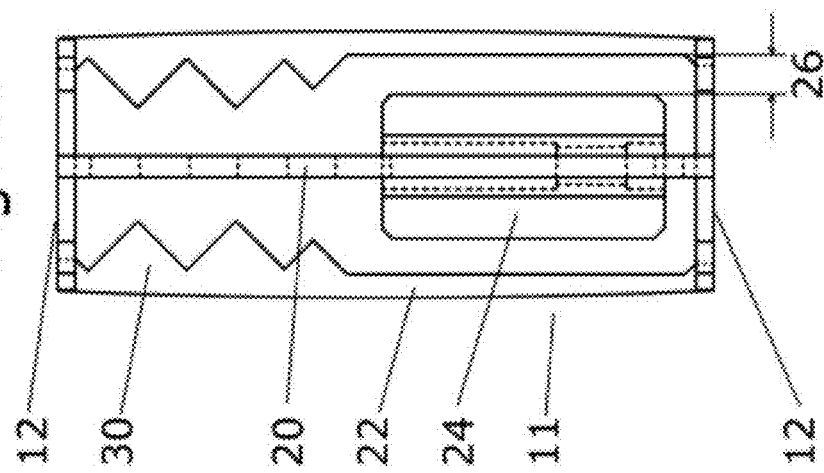

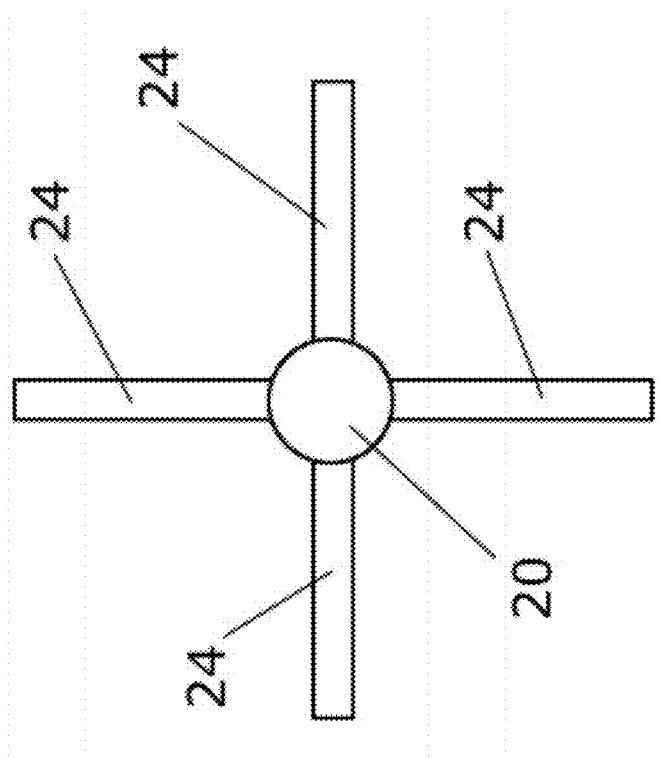

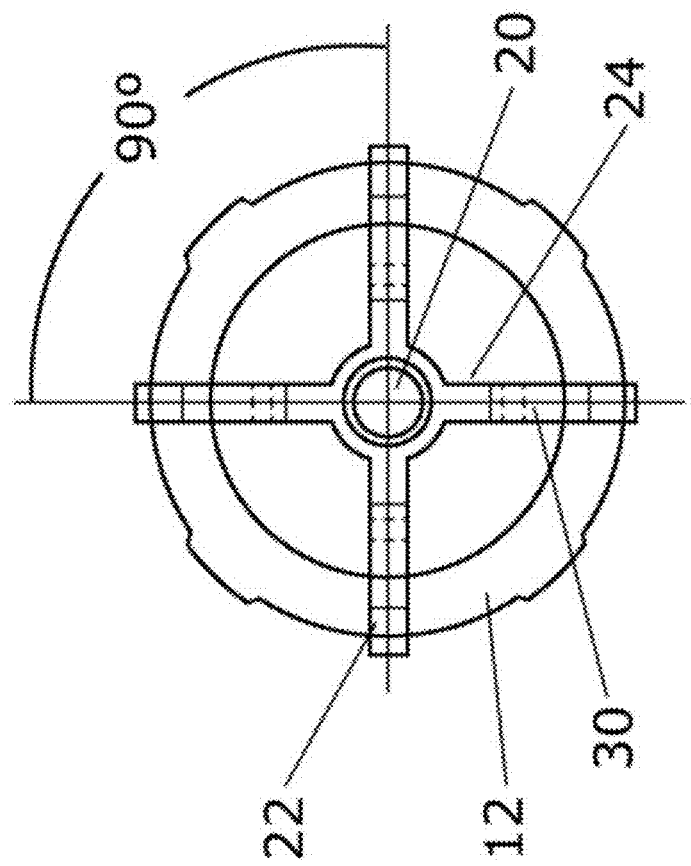

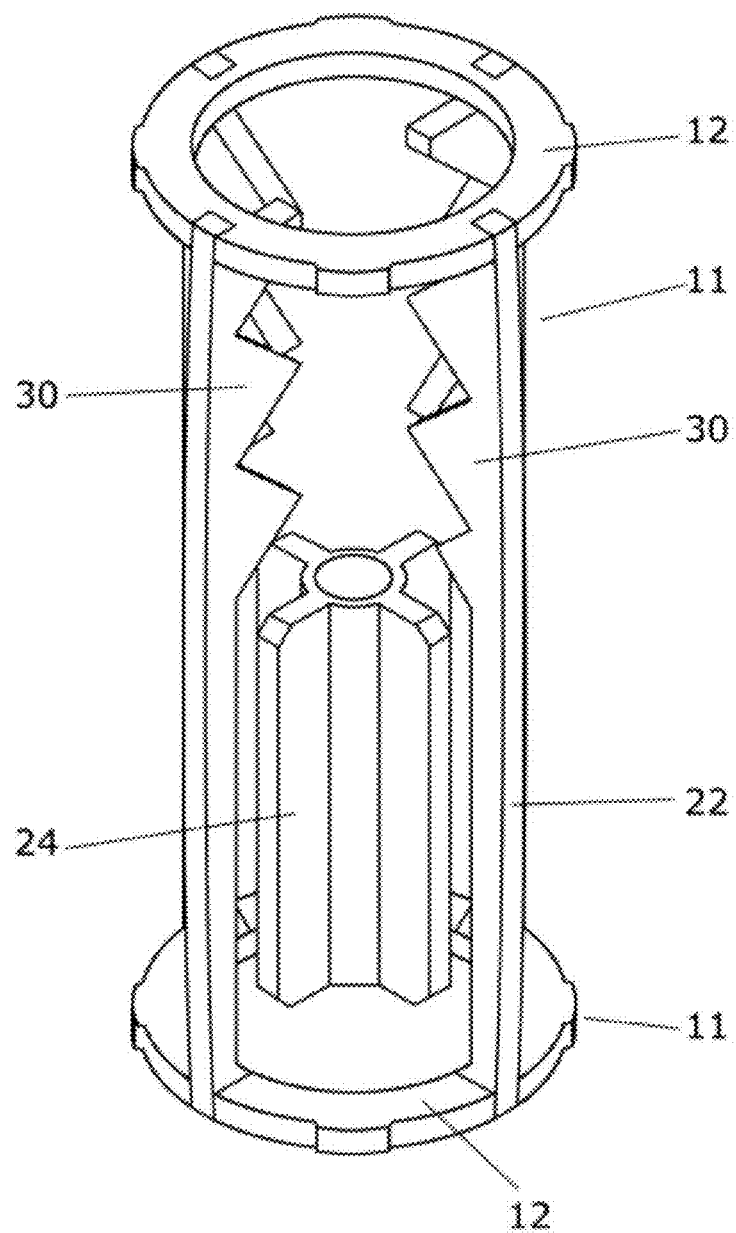

APPARATUS AND METHOD FOR MEASURING RHEOLOGICAL PROPERTIES OF A FLUID CONTAINING PARTICULATE

FIELD

The invention generally relates to devices and methods used to test the rheology of fluids, such as the viscosity, elasticity, and consistency of fluids, especially fluids containing suspended particulate materials. The particular field of use is the oil and gas industry.

BACKGROUND

Various types of fluids can be used in the oil and gas industry. Non-limiting examples include drilling muds, cements, gravel slurries, and stimulation treating fluids. Such fluids can be pumped into oil or gas wells in ways known in the industry. It is desirable to know the various characteristics of these fluids to determine how they will act while being pumped and placed in, or circulated through, the wells.

Rheology is the branch of physics dealing with the deformation and flow of matter. Viscosity, elasticity, and consistency are rheological characteristics that sometimes need to be measured for a given fluid. Such rheological characteristics can be non-linear functions of variables such as time, temperature, and pressure. Known devices used to test fluids for these characteristics include viscometers, rheometers, and consistometers.

In the oil and gas industry fluids containing suspended particulate can be used. These fluids can be in a gel form to better support the particulate. The particulate is typically referred to as proppant, and consists of sized particles mixed within a fluid, such as a fracturing fluid. In addition to naturally occurring sand grains, man-made or specially engineered proppants, such as resin-coated sand, glass beads, or high-strength ceramic materials like sintered bauxite, may also be used. Proppant materials can be sorted for size and sphericity to provide an efficient conduit for production of fluid from the reservoir to the wellbore once placed in the formation. Proppants can vary in size from powder to sandy.

The treatment of subterranean formations penetrated by a well bore to stimulate the production of hydrocarbons or the ability of the formation to accept injected fluids has long been known in the art. One of the most common methods of increasing productivity of a hydrocarbon-bearing formation is to subject the formation to a fracturing treatment. This treatment is effected by injecting a gas, liquid, or two-phase fluid down the well bore at sufficient pressure and flow rate to fracture the subterranean formation. Continued pumping of the fracturing fluid containing proppant into the fracture results in placement of the proppant within the fracture. Following the treatment, the fracturing fluid is recovered from the well bore or permitted to migrate from the fracture leaving the propping agent remaining in the fracture. The propping agent prevents the complete closure of the fracture to provide a flow channel through which an increased quantity of a hydrocarbon or other fluid can flow.

For fluids that carry proppants, it is desirable that the proppant be suspended in the fluid for a length of time before settling. For this reason the fluid is most commonly used in a gelled form. Several factors, such as heat and length of time, will contribute to the loss of suspension, due to the gelled fluid melting or breaking down. The characteristics such as viscosity, elasticity, and consistency of the fluid are important rheological characteristics that contribute to the suspension of the particulate in the fluid, and these characteristics, and the rate of degeneration of these characteristics, must be measured in these fluids.

A typical fluid used to transport proppant has a viscosity that changes during the time the fluid is used in a well. Viscosity is defined as the ratio of shear stress to shear rate (velocity gradient). If this ratio changes with shear rate, this may be referred to as "apparent viscosity function." Viscosity is one parameter of the fluid that defines the fluid's ability to support the proppant in suspension. However, to measure a single viscosity point or the apparent viscosity function does not directly indicate the time during which the fluid will support proppant in suspension and the time during which the fluid will not. That is, a measurement that merely shows a changing viscosity does not indicate when the particulate is in suspension within the fluid and when it is not (i.e., when the proppant has settled out of the fluid). Thus, there is the need for a device and method which can test fluids to determine times during which proppant is suspended in the fluid and times during which proppant settles out of suspension. There is the more particular need for a device and method to measure the viscous and elastic properties of a fluid, both with and without proppant, under dynamic conditions at elevated temperatures and pressures at a variety of shear rates and in such a way as to directly indicate particle transport, suspension and settling. At least one embodiment of such a device and method desirably should also be suitable for use at a well site to measure crosslink time of a fluid being pumped into the well.

SUMMARY

An embodiment of the present invention is an apparatus for testing a rheological property of a fluid containing particulate. The apparatus having a receptacle having a cylindrical sidewall enclosed by a bottom wall defining an axis and a cavity for receiving the fluid containing particulate to be tested. At least two inward projections extend inward from the cylindrical sidewall defining a first radial distance from the axis. An axial support can be positioned in the cavity of the receptacle that has at least two outward projections extending outward from the axial support defining a second radial distance from the axis. The second radial distance, from the center axis to the edge of the outward projections, is less than the first radial distance, from the center axis to the edge of the inward projections, thereby the projections do not extend past each other and do not touch each other when passing by each other. Relative rotational motion can be imparted to the receptacle and the axial support such that the inward projections and outward projections can impart a stirring force in the fluid containing particulate. At least one of the receptacle or axial support is capable of generating a measurement signal in response to torque forces created from movement of the fluid containing particulate within the receptacle upon the relative rotational motion between the receptacle and the axial support.

The apparatus can include an annular ring on the axial support above outward projections to reduce foaming or fluid movement up the axial support. The relative rotational motion can be imparted by rotational motion of the receptacle and the axial support can be capable of generating a measurement signal, such as an electrical signal, in response to torque forces created from movement of the fluid containing a particulate within the receptacle impinging on the axial support.

The inward projections can include an inner edge that has a substantially constant distance from the axis. The outward projections can include an outer edge that has a substantially constant distance from the axis. Thereby the inward projections and outward projections are not in an interlinking relationship as opposing flag type projections typically have.

The apparatus can include a cage positioned within the receptacle having the at least two inward projections. The cage can be inserted and removed from the receptacle and can be attached to the receptacle by frictional pressure exerted on the sidewall by the cage. The receptacle can include a removable end portion forming the bottom wall that can be used for the insertion and removal of the cage.

The apparatus can include at least two secondary inward projections extending inward from the cylindrical sidewall at a location above the inward projections and the outward projections. Portions of the secondary inward projections can extend closer to the axis than the inward projections and can impart shear forces on the fluid containing particulate. The secondary inward projections can include an inner edge of varying distance from the axis, such as with flag type projections. The secondary inward projections can be included in the removable cage.

The receptacle and axial support can be capable of attachment to a viscometer, such as a Fann Model 50, Ametek Chandler Model 5550 or a Grace Model M5600. In an embodiment the receptacle can have an interior diameter of between 0.5 to 4.0 inches, optionally from 1.35 to 1.55 inches. In an embodiment the inward projections can extend inward from the cylindrical sidewall from 0.1 to 2.0 inches, optionally from 0.1 to 0.5 inches. In an embodiment the outward projections can extend outward from the axis from 0.1 to 2.0 inches, optionally from 0.15 to 0.35 inches.

Another embodiment of the present invention is a method of testing a rheological property of a fluid containing particulate. The method involves placing a sample of the fluid containing particulate in an embodiment of the apparatus of the present invention. Relative rotational movement is created between the receptacle and the axial support such that the inward projections and outward projections impart a stirring force in the fluid containing particulate.

A measurement signal, such as an electrical signal, is generated in response to torque forces created from movement of the fluid containing particulate within the receptacle, such as on the axial support for example. The signal is analyzed to determine the onset of particulate settling by detecting an increase in the torque, whereby elastic particulate transport occurs during a period of time before the onset of particulate settling, and viscous settling occurs during a period of time after the onset of particulate settling.

The increase in the torque can be characterized by an upward inflection in a graph of the torque versus time. The period of elastic particulate transport occurring near the onset of particulate settling can be characterized by a substantially constant torque.

The method can further include increasing pressure in the connected receptacle such that pressure on the fluid containing particulate in the receptacle is greater than atmospheric pressure and heating the fluid containing particulate in the receptacle to a temperature greater than ambient temperature.

BRIEF DESCRIPTION OF DRAWINGS

FIG. 1 is a block diagram of a viscometer having a modified test cell implementing a preferred embodiment of the present invention, which viscometer is illustrated in an environment at an oil or gas well site and which viscometer can be an open-cup type or a high-pressure and/or high-temperature type.

FIG. 2 is a schematic illustration of an embodiment of the present invention.

FIG. 3a is a representation of another configuration of the present invention showing outward projections from an axial support and inward projections from a support cage.

FIG. 3b is a representation of another configuration of the present invention showing outward projections from an axial support and inward projections from a support cage.

FIG. 4 is a plan view representation of four projections spaced around an axial support.

FIG. 5 is a plan view representation of four outward projections spaced around an axial support and four inward projections spaced around a support cage.

FIG. 6 illustrates a perspective view of a configuration of the present invention showing outward projections from an axial support and inward projections from a support cage.

DETAILED DESCRIPTION

Figure 7:
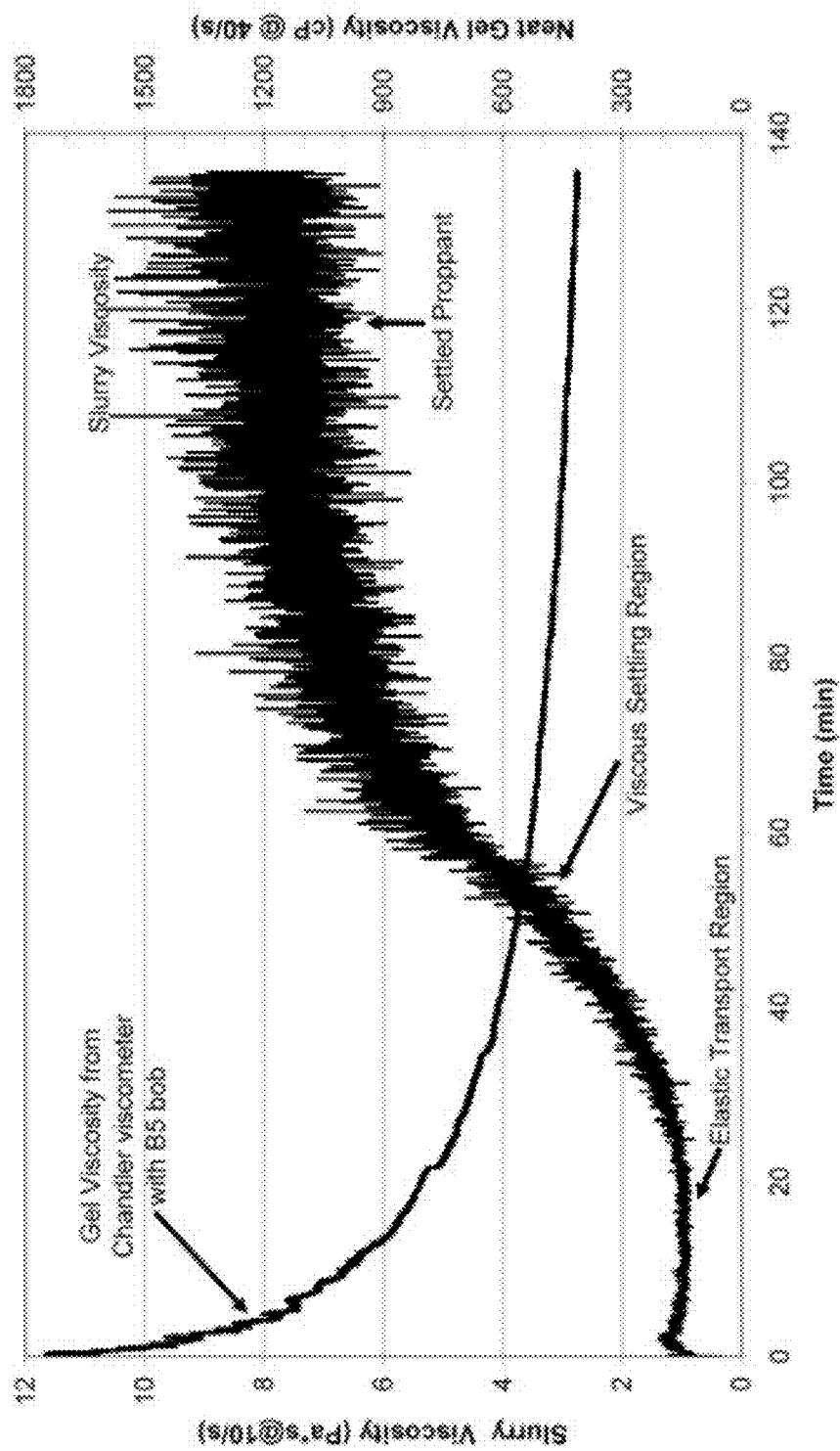
FIG. 7 is a graphical representation of gel viscosity measurement and particle transport capability measurement in accordance with the method of the present invention, for a particular example of a viscosified fluid.

The present invention includes a testing chamber with a rotor and stator, with vanes protruding from both, with a means to apply a constant rotational velocity and to measure the torque produced via a signal. The device operates by applying a rotation to the rotor, which creates a rotational vortex within the testing chamber. The number of vanes and speed of rotation may vary according to design to better match the properties, such as the average shear rates and suspension under volume of fracturing fluids used in the oil and gas industry. A desirable shear rate can range from 1 to 100 $sec^{-1}$. Optional shear rates can range from 1 to 75 $sec^{-1}$, from 1 to 50 $sec^{-1}$, and from 1 to 25 $sec^{-1}$.

U.S. Pat. No. 6,782,735 to Walters et al and U.S. Pat. No. 7,392,842 to Morgan et al, both incorporated herein by reference, show designs of viscometers with interpenetrating 'flag' vanes attached to the rotor and stator of a viscometer. In large sized cups the devices worked well, but when scaled smaller for adaption to smaller cups typical of commercially available viscometers, such as the Fann Model 50 and Chandler Model 5550, the signals became erratic as the proppant settled, which was problematic.

The present invention addresses this issue by altering the vane design on the rotor and stator device. The new device can provide more accurate readings even when scaled to a smaller size of standard, commercially available viscometers. The device has a simpler, less geometrically complex design and allows for more accurate testing conditions of fluid containing particulate. The device described in this invention can be used with commercially available viscometers, reducing the need for custom-designed cups in most cases. Other advantages include access points on the cup such as lids and screw caps, and modular cage designs allowing for faster and more efficient flushing and cleaning of the test chamber between tests. The device allows for more accurate testing of fracturing fluid in a working environment since the fluid can be tested while already mixed, as it is when pumped into a well to be fractured.

The rotor and stator vanes in this particular embodiment have a substantially straight-edge design which do not interpenetrate with the vanes on the other. Optionally secondary vanes on the rotor can vary in shape, provided the section that rotates around the stator has a straight-edge design. The secondary vanes can have straight, flag-shaped, or other angled shapes that can help to create shear, which can be beneficial with certain fluid mixtures.

A type of fluid with which the present invention can be used is referred to as a viscous and/or elastic fluid whose viscosity changes over time. One such fluid is a viscoelastic fluid that may typically go through different phases over time; for example, from an initial uncrosslinked state, to a crosslinked elastic state, to a viscous settling state. The particulate to be used in the fluid can be, for example, sized sand, resin coated sand, sintered bauxite beads, metal beads or balls, ceramic particles, glass beads, polymer resin beads, ground nut shells and the like. The particulate size may be of any suitable size, with typical sizes being within the range from about 8 to about 170 on the U.S. Sieve Series scale. The foregoing are non-limiting examples.

A more general statement about a mixture for which the present invention is particularly intended is that it is a mixture of a particulate and a fluid which during one period of time is able to support the quantity of particulate in suspension under a stirring action but which during another period of time is unable to support the particulate in suspension even under the stirring action. The invention can also measure viscous and/or elastic properties of the fluid itself without sand. Examples of fluids containing particulate include drilling muds, cement slurries, and stimulation treating fluids used in the oil and gas industry.

An embodiment of the present invention is an apparatus for testing a rheological property of a fluid containing particulate. The apparatus has a receptacle having a cylindrical sidewall enclosed by a bottom wall defining a cavity for receiving the fluid containing particulate to be tested. The receptacle has a center axis from which the various dimensions of the invention can be referred to. At least two inward projections extend inward from the cylindrical sidewall defining a first radial distance from the axis. An axial support that can be positioned in the cavity of the receptacle has at least two outward projections extending outward from the axial support defining a second radial distance from the axis. The second radial distance, from the center axis to the edge of the outward projections, is less than the first radial distance, from the center axis to the edge of the inward projections, thereby the projections do not touch each other. Relative rotational motion can be imparted to the receptacle and the axial support such that the inward projections and outward projections can impart a stirring force in the fluid containing particulate. At least one of the receptacle or axial support is capable of generating a measurement signal in response to torque forces created from movement of the fluid containing particulate within the receptacle upon the relative rotational motion between the receptacle and the axial support.

The apparatus can also include an annular ring on the axial support above outward projections to reduce foaming or fluid movement up the axial support. The relative rotational motion can be imparted by rotational motion of the receptacle and the axial support can be capable of generating a measurement signal, such as an electrical signal, in response to torque forces created from movement of the fluid containing a particulate within the receptacle impinging on the axial support.

The inward projections can include an inner edge that has a substantially constant distance from the axis. The outward projections can include an outer edge that has a substantially constant distance from the axis. Thereby the inward projections and outward projections are not in an interlinking relationship as opposing flag type projections would have.

The apparatus can include a cage positioned within the receptacle having the at least two inward projections. The cage can be inserted and removed from the receptacle and in an embodiment can be attached to the receptacle by frictional pressure exerted on the sidewall by the cage. The receptacle can include a removable end portion forming the bottom wall that can be used for the insertion and removal of the cage. In an alternate embodiment the cage can be attached by mechanical means, such as a set screw or a threaded connection between the cage and receptacle.

The apparatus can include at least two secondary inward projections extending inward from the cylindrical sidewall at a location above the inward projections and the outward projections. Portions of the secondary inward projections can extend closer to the axis than the inward projections and can impart shear forces on the fluid containing particulate. The secondary inward projections can include an inner edge of varying distance from the axis, such as with flag type projections. The secondary inward projections can be included in the removable cage.

The receptacle and axial support can be capable of attachment to a viscometer, such as a Fann Model 50, Ametek Chandler Model 5550 or a Grace Model M5600. In an embodiment the receptacle can have an interior diameter of between 0.5 to 4.0 inches, optionally from 1.35 to 1.55 inches. In an embodiment the inward projections can extend inward from the cylindrical sidewall from 0.1 to 2.0 inches, optionally from 0.1 to 0.5 inches. In an embodiment the outward projections can extend outward from the axis from 0.1 to 2.0 inches, optionally from 0.15 to 0.35 inches.

Another embodiment of the present invention is a method of testing a rheological property of a fluid containing particulate. The method involves placing a sample of the fluid containing particulate in a receptacle having a cylindrical sidewall enclosed by a bottom wall defining an axis. The receptacle has at least two inward projections extending inward from the cylindrical sidewall. The inward projections have an inner edge of substantially constant distance from the axis, the inner edge defining a first radial distance from the axis.

The receptacle is connected to a viscometer having an axial support adapted to be positioned in the cavity of the receptacle, the axial support having at least two outward projections extending outward from the axial support. The outward projections have an outer edge of substantially constant distance from the axis that define a second radial distance from the axis. Relative rotational movement is created between the receptacle and the axial support by rotational motion of the receptacle such that the inward projections and outward projections impart a stirring force in the fluid containing particulate.

A measurement signal, such as an electrical signal, is generated in response to torque forces on the axial support created from movement of the fluid containing particulate within the receptacle. The signal is analyzed to determine the onset of particulate settling by detecting an increase in the torque, whereby elastic particulate transport occurs during a period of time before the onset of particulate settling, and viscous settling occurs during a period of time after the onset of particulate settling.

The increase in the torque can be characterized by an upward inflection in a graph of the torque versus time. The period of elastic particulate transport occurring near the onset of particulate settling can be characterized by a substantially constant torque.

The relative rotational movement between the receptacle and the axial support can be substantially constant for a period of time before the onset of particulate settling. The fluid can be a gel and the particulate can be a sand. Substantially all the sand can remain suspended in the gel during the period of elastic particulate transport, and substantially all the sand can settle out of the gel during the period of viscous settling. The method can include analyzing the measurement signal to determine a crosslinking time for the gel.

The method can further include increasing pressure in the connected receptacle such that pressure on the fluid containing particulate in the receptacle is greater than atmospheric pressure and heating the fluid containing particulate in the receptacle to a temperature greater than ambient temperature. In an embodiment the receptacle can have an interior diameter of between 0.5 to 4.0 inches, optionally from 1.35 to 1.55 inches. In an embodiment the inward projections can extend inward from the cylindrical sidewall from 0.1 to 2.0 inches, optionally from 0.1 to 0.5 inches. In an embodiment the outward projections can extend outward from the axis from 0.1 to 2.0 inches, optionally from 0.15 to 0.35 inches.

One embodiment of the present invention that tests a fluid such as described above is implemented with a high-pressure (above ambient), high-temperature (above 212° F.) viscometer which includes a receptacle to receive the fluid to be tested and which also includes a support that is disposed in the receptacle (and thus also in the fluid) when the fluid is in the receptacle to be tested. Such a viscometer can be a conventional one (e.g., a Fann model 50 viscometer) but adapted to the present invention by a modified test cell 2. The present invention can also be used with, or incorporate, a conventional open-cup or atmospheric viscometer (e.g., a Fann model 35 viscometer), but also adapted by a modified test cell 2. In either case, this modified test cell 2 includes at least one projection extending laterally inward from an inner surface of the receptacle and forming part of the modified test cell 2. The modified test cell 2 can also included at least two projections extending laterally outward from the support. Such device of the present invention is depicted in FIG. 1 and can otherwise comprise conventional components of a high-pressure, high-temperature viscometer, including pressure control 4, temperature control 6, and readout 8, or of an atmospheric type viscometer that does not have at least the pressure control 4. As also shown in FIG. 1, either embodiment can be used at a well site to receive in real time a sample of the mixture from a fluid stream 7 flowing into an oil or gas well 9. In addition, the test cell 2 can also receive a sample of the proppant 5 for mixing with a sample of the fluid stream 7 and testing the rheological properties of the mixture.

FIG. 2 represents a particular embodiment of a modified test cell 2 for high-pressure use. A test cell 2 includes a conventional slurry cup receptacle 10 of a conventional viscometer of the high-pressure, high-temperature type referred to above. The slurry cup 10 holds a cylindrical support cage 11 with multiple support structures 12 extending from an end closed by a bottom wall 14 to an open end opposite the bottom wall 14. The cage 11 and the bottom wall 14 have inner surfaces defining a cavity 16 inside the slurry cup 10. The cavity 16 receives the fluid to be tested. This cavity 16 provides a single continuous volume or cell for the fluid to be tested.

The modified test cell 2 of the FIG. 2 embodiment also includes means for closing the open end of the cavity 16 or slurry cup 10 after the fluid is placed in the cavity 16. This closing means completes the definition of the outer boundaries of the continuous test chamber, which can be pressurized above atmospheric pressure. In the implementation of FIG. 2, the closing means includes a conventional pressure sealed end closure 18 for the slurry cup 10 defining the cavity 16. The closing means also includes a support, which in the FIG. 2 implementation is an axial shaft, or axial support 20. This axial shaft hangs below the end closure 18 into the slurry cup 10 when the end closure 18 is connected to the slurry cup 10 in conventional manner to close the slurry cup 10. One example of the end closure 18 and the axial shaft 20 is found in the Fann Model 50 viscometer; however, other high-pressure, high-temperature devices can be used.

The modified test cell 2 shown in FIG. 2 further includes means for stirring fluid in the test chamber such that particulate in the fluid is suspended in the fluid during one period of time of the stirring but is not suspended in the fluid during another period of time of the stirring. This is implemented in FIG. 2 by at least one projection extending into the cavity 16 from the inner surface of the support cage 11. In FIG. 2, a plurality of substantially straight-edged projections 22 are connected to the inner surface of the support cage 11 diametrically opposite each other. Connection can be by any suitable means, including but not limited to welding to or integrally machining with the support structures 12. In another embodiment the support cage 11, containing the support structures 12 and projections 22, can be frictionally attached to the inner wall of the slurry cup 10. The bottom wall 14 can be removable from the slurry cup 10, enabling the support cage 11 containing the support structures 12 and projections 22 to be inserted or removed from the slurry cup 10.

The FIG. 2 implementation also includes at least two projections extending laterally outward from the axial support 20, desirably in a rotationally balanced configuration and positioned to have desired sensitivity to settling particulate. Two diametrically opposed, axially spaced projections 24 of substantially rectangular-shaped metallic projections are connected to the axial shaft 20 in the FIG. 2 embodiment. While there may be a plurality of projections 24, in one embodiment there is an even number of these projections. Connection can be by any suitable means, including but not limited to welding to or integrally machining with the axial support 20 or a mandrel that connects to the axial support 20.

The projections 22, 24 are large enough to generate a torque during stirring, but small enough to produce a torque reading within a desired range (the larger the projections, the larger the torque reading) and to leave a gap 26 between the set of projections 22 and the set of projections 24 sufficient for the particulate material to pass through without bridging (e.g., three to four particle diameters).

The projections 24 operatively cooperate with the projections 22 to effect stirring of fluid in the slurry cup 10 in response to rotation of at least one of the slurry cup 10 or axial support 20. Typically the slurry cup 10 is rotated so that the projections 22 principally effect the stirring, and the projections 24 are deflected in response to thereby sense torque. This rotation is achieved in conventional manner within the remainder of the viscometer used to implement the described embodiment of the present invention. The rotation to be imparted is such that mixing of the particulate in suspension within the fluid occurs during a period of the stirring time in which the fluid is still able to support the particulate, but the rotation is not such that mixing occurs when the fluid is no longer able to support the particulate in suspension, whereby the particulate settles out of suspension. The rotation is also obtained in a manner that permits an appropriate readout signal to be generated. Such rotation is typically within the range between one revolution per minute and one thousand revolutions per minute. In an embodiment the slurry cup 10 interior diameter is from 0.5 to 4.0 inches, or optionally from 1.35 to 1.55 inches. The inward projections 22 can range from 0.05 to 2.0 inches, optionally from 0.1 to 0.5 inches. The outward projections 24 can range from 0.1 to 2.0 inches, optionally from 0.15 to 0.35 inches.

The embodiment of the present invention shown in FIG. 1 includes a readout 8. This is part of a means for generating a signal in response to the stirring of the fluid during both the time period while particulate suspension occurs and the time period during while particulate settling occurs. This can be implemented in FIG. 2 by using the two or more projections 24 on the axial shaft 20. For example, when the slurry cup 10 is rotated, torque can be sensed through the axial shaft 20 in known manner. In an embodiment in which the axial shaft 20 is rotated to effect mixing by the projections 24, torque can be sensed through the slurry cup 10 in known manner. For the modified test cell 2 of the illustrated embodiment, the sensitivity of the readout 8 to such torque can be adjusted by using different strengths of springs or different sizes of projections or different transducers. For example, for a Fann Model 50 viscometer, a lighter weight spring may be used in the present invention as compared to a spring used in a conventional viscometer construction and operation. An electric signal can be generated in known manner in response to the deflection of the axial shaft 20 and the electric signal can be used in known manner to create a display, such as an electronic display or a printed graph. The display can be maintained so that a graph of the response over time is obtained in accordance with the present invention, which can be used to analyze rheological properties of a fluid containing particulate.

The projections 22, 24 and their inter-relationships with each other and the overall viscometer and method of the present invention can take different configurations. Some examples are represented in FIGS. 3a and 3b. FIGS. 3a and 3b show examples of a support cage 11 and axial support 20 combinations. The respective projections 24 extending from the respective axial support 20 are axially aligned along the axial support 20, and the respective projections 22 extend from the support structures 12, which run up along the support cage 11. The projections 22 would be adjacent to the interior sidewall of the slurry cup 10 (not shown). The projections 22 can be flared or bowed as indicated on FIG. 3B, see 28a, 28b. The bowed shape of the projections 22 can facilitate the insertion and frictional attachment of the support cage 11 into the slurry cup 10 (not shown).

The support cage 11 can further include angled vane projections 30 above the projections 22 at a distance 32 above the projections 24 on the axial support 20. The angled vane projections 30 can project further towards the axial support 20 than the projections 22. The angled vane projections 30 can provide shear forces onto the fluid being tested and can facilitate the induced rotational motion of the fluid being tested if the relative rotational motion is achieved from the rotational motion of the slurry cup 10 (not shown) and therefore the support cage 11. FIG. 3a shows these angled vane projections 30 with full vanes running from top to bottom, with a half vane at the bottom of the section of angled vane projections 30. FIG. 3b shows the angled vane projections 30 with full vanes running from bottom to top, with a half vane at the top of the section of angled vane projections 30. The invention may include one or more of the projection 22 styles shown in FIGS. 3a and 3b, possibly in conjunction with one another. In one embodiment the support cage 11 can include support structures 12 on the top and bottom of the support cage 11, four projections 22 attached to the support structures 12 and four angled vane projections 30 attached to and located above the projections 22. One set of projections 22 and angled vane projections 30 on opposing sides of the support cage 11 have the shape as shown in FIG. 3a while the other set of projections 22 and angled vane projections 30 on opposing sides of the support cage 11 have the shape as shown in FIG. 3b. The alternating pattern of the angled vane projections 30 as they are rotated within a fluid filled slurry cup 10 (not shown) will provide a tortuous path for the fluid and impart stirring and shear forces to the fluid.

FIG. 4 illustrates an embodiment of the axial shaft 20 having four projections 24 equally spaced around the axial shaft 20.

FIG. 5 illustrates an overhead view of FIG. 3a of the support cage 11 and axial shaft 20 with their respective projections. The view of FIG. 5 is when the axial shaft 20 and its projections 24 are aligned with the support structures 12 and its projections 22. Four projections 24 are equally spaced around the axial shaft 20, and four projections 22 are equally spaced around the inside of the support structures 12. The overlap of the angled vanes on projections 22 and the projections 24 is shown. In the embodiment illustrated by FIG. 5 the angle between adjacent projections 22 is substantially 90°.

FIG. 6 illustrates a perspective view of an embodiment of the support cage 11 and projections 24 extending from the axial shaft (not shown). A cylindrical support cage 11 having two support structures 12 on either end and projections 22, 30 extending from the top support structure 12 to the bottom support structure 12. Four projections 24 extending axially from a support shaft (not shown). In this embodiment the four projections 24 extend from the axial support (not shown) and four respective projections 22 extend from the support structures 12, which run up along the support cage 11 along with angled vane projections 30 at the top.

The projections 24 operatively cooperate with the projections 22 to effect stirring of a fluid in a slurry cup. Typically the slurry cup (not shown) is rotated so that the projections 22 principally effect the stirring, and the projections 24 are deflected in response to thereby sense torque. This rotation can be achieved in conventional manner within the remainder of the viscometer used to implement the described embodiment of the present invention. Such rotation is typically within the range between one revolution per minute and one thousand revolutions per minute.

An embodiment of the present invention provides a method of testing a viscosified fluid containing particulate. The method includes using a viscometer, such as a high-pressure, high-temperature viscometer, a container having at least two inward projections. It also includes using in the viscometer an axial support or axial shaft having at least two outward projections. The container, also called a slurry cup, holds the fluid to be tested, and the axial support extends into the fluid. The method further comprises creating relative movement between the container and the axial support, and the projections thereof. At least one set of these projections imparts a stirring force in the fluid. Relative movement is created by rotating in known manner either the slurry cup of the viscometer or the axial support of the viscometer. The method includes generating a measurement signal in response to torque forces resulting from the relative movement. The measurement signal can be an electric signal generated in response to torque related to creating relative movement between the container and the axial support and the projections thereof. Such electric signals can be generated with conventional torque sensing components of the viscometer that respond to deflection of the axial shaft, by the force of the fluid against the projections on the axial shaft. Alternatively, the axial deflection may be read directly on a dial without the use of an electrical signal or signal generating means. Another aspect of the foregoing is that the relative movement is created for a time during which the viscosity and/or elasticity of the fluid changes, which time includes a first period during which substantially all the particulate suspended in the fluid and which time includes a second period during which substantially all the particulate settles out of suspension in the fluid (such as due to the viscosity and/or elasticity of the fluid decreasing to a level which does not support the particulate). That is, rotation (e.g., by a motor connected and operated in known manner) continues throughout the range of viscosity change from the first period through the second period. Thus, the measurement signal taken over time has a characteristic that indicates the first period (an elastic particulate transport time period) and the second time period (a viscous settling time period). The measurement signal can also indicate crosslinking that occurs in the fluid or indicate crosslink degradation changing the viscoelastic properties of the fluid.

As apparent from the description of the invention above, stirring can include either (1) rotating the slurry cup relative to a support disposed in the fluid, wherein the slurry cup has at least two projections extending inward into the fluid from the slurry cup and the support has at least two projections extending outward into the fluid from the support, or (2) rotating the support disposed in the fluid relative to the slurry cup. The former can be desirable due to the lighter mass of the axial shaft structure relative to the slurry cup structure.

EXAMPLES

Referring to FIG. 7, the viscosity of a cross-linked gel test fluid without sand and a slurry of cross-linked gel having 8 lb/gal of 20/40 mesh ceramic particulate is graphed over time, indicating an elastic transport region, a viscous settling region and a settled proppant region. Both were tested at 75° F.

There is a decrease with time in the viscosity of the cross-linked gel fluid with breaker. This curve is typical for viscosity decline and it shows no indication of whether or not the gel will support sand. The cross-linked gel slurry supports sand and has minimal resistance to flow for a period of time (about 30 minutes). This is the period of elastic transport, or perfect particulate transport, where any settling is offset by the motion of the rotating slurry cup 10 and the interacting projections 22, 24 as shown in FIG. 2. There is a slight decrease in resistance (from about 5-20 minutes) due to the decrease in viscosity of the supporting gel. At the end of the elastic transport region, an upward inflection indicates the onset of particulate settling. Beyond this point, the gel fluid loses its elasticity, and particulate settling behavior is like that in non-crosslinked fluids and is controlled by viscous effects rather than elasticity. The viscous settling region described above and illustrated in FIG. 7 can be calibrated or compared by measuring the slopes of non-crosslinked linear gel fluids containing a similar concentration of the sand or other particulate. Data used to make FIG. 7 is shown in Table 1 below.

TABLE 1

25 ppt CMHPG
1.0 gpt Zr crosslinker
2.5 ppt Enzyme breaker
8 ppg EconoProp 20/40

| Time (min) | Visc (Pa·s) | Shear Rate (1/s) | Temperature (F.) |
|---|---|---|---|
| 1 | 1.91 | 7.0 | 74.8 |
| 2 | 1.90 | 7.0 | 75.5 |
| 3 | 1.82 | 7.0 | 75.9 |
| 4 | 1.92 | 7.0 | 76.0 |
| 5 | 1.95 | 7.0 | 76.2 |
| 6 | 2.03 | 7.0 | 76.2 |
| 7 | 1.94 | 7.0 | 76.2 |
| 8 | 1.71 | 7.0 | 76.0 |
| 9 | 1.59 | 7.0 | 76.0 |
| 10 | 1.59 | 7.0 | 76.2 |
| 11 | 1.66 | 7.0 | 76.2 |
| 12 | 1.71 | 7.0 | 76.0 |
| 13 | 1.65 | 7.0 | 76.0 |
| 14 | 1.48 | 7.0 | 76.0 |
| 15 | 1.88 | 7.0 | 76.0 |
| 16 | 1.75 | 7.0 | 76.0 |
| 17 | 1.73 | 7.0 | 76.0 |
| 18 | 1.70 | 7.0 | 76.0 |
| 19 | 1.86 | 7.0 | 76.0 |
| 20 | 1.68 | 7.0 | 75.9 |
| 21 | 1.59 | 7.0 | 75.9 |
| 22 | 1.55 | 7.0 | 75.9 |
| 23 | 1.63 | 7.0 | 75.9 |
| 24 | 1.57 | 7.0 | 75.9 |
| 25 | 1.71 | 7.0 | 75.9 |
| 26 | 1.61 | 7.0 | 75.9 |
| 27 | 1.50 | 7.0 | 75.9 |
| 28 | 1.61 | 7.0 | 75.9 |
| 29 | 2.00 | 7.0 | 75.9 |
| 30 | 1.84 | 7.0 | 75.9 |
| 31 | 1.76 | 7.0 | 75.9 |
| 32 | 1.80 | 7.0 | 75.9 |
| 33 | 1.67 | 7.0 | 75.9 |
| 34 | 1.63 | 7.0 | 75.9 |
| 35 | 1.59 | 7.0 | 75.9 |
| 36 | 1.69 | 7.0 | 75.7 |
| 37 | 1.62 | 7.0 | 75.7 |
| 38 | 1.74 | 7.0 | 75.7 |
| 39 | 1.84 | 7.0 | 75.7 |
| 40 | 1.62 | 7.0 | 75.9 |
| 41 | 1.76 | 7.0 | 75.9 |
| 42 | 1.85 | 7.0 | 75.9 |
| 43 | 1.67 | 7.0 | 75.7 |
| 44 | 1.60 | 7.0 | 75.9 |
| 45 | 1.86 | 7.0 | 75.9 |
| 46 | 1.60 | 7.0 | 75.9 |
| 47 | 1.73 | 7.0 | 75.7 |
| 48 | 1.73 | 7.0 | 75.7 |
| 49 | 1.77 | 7.0 | 75.7 |
| 50 | 1.90 | 7.0 | 75.7 |
| 51 | 1.63 | 7.0 | 75.7 |
| 52 | 1.90 | 7.0 | 75.7 |
| 53 | 1.43 | 7.0 | 75.7 |
| 54 | 1.58 | 7.0 | 75.7 |
| 55 | 1.72 | 7.0 | 75.7 |
| 56 | 2.02 | 7.0 | 75.7 |
| 57 | 1.67 | 7.0 | 75.7 |
| 58 | 2.05 | 7.0 | 75.7 |
| 59 | 2.14 | 7.0 | 75.7 |
| 60 | 1.84 | 7.0 | 75.7 |
| 61 | 1.98 | 7.0 | 75.7 |
| 62 | 2.15 | 7.0 | 75.7 |
| 63 | 1.88 | 7.0 | 75.7 |
| 64 | 2.07 | 7.0 | 75.7 |
| 65 | 1.66 | 7.0 | 75.7 |
| 66 | 1.92 | 7.0 | 75.7 |
| 67 | 1.81 | 7.0 | 75.7 |
| 68 | 2.05 | 7.0 | 75.7 |
| 69 | 1.79 | 7.0 | 75.5 |
| 70 | 1.98 | 7.0 | 75.7 |
| 71 | 2.08 | 7.0 | 75.7 |
| 72 | 2.33 | 7.0 | 75.5 |
| 73 | 1.74 | 7.0 | 75.7 |
| 74 | 2.12 | 7.0 | 75.7 |
| 75 | 2.24 | 7.0 | 75.3 |
| 76 | 1.95 | 7.0 | 75.5 |
| 77 | 2.43 | 7.0 | 75.5 |
| 78 | 2.39 | 7.0 | 75.5 |
| 79 | 2.15 | 7.0 | 75.5 |
| 80 | 2.35 | 7.0 | 75.3 |
| 81 | 2.20 | 7.0 | 75.5 |
| 82 | 2.15 | 7.0 | 75.3 |
| 83 | 2.42 | 7.0 | 75.3 |

TABLE 1-continued

| Time (min) | Visc (cP) | Shear Rate (1/s) | Temperature (F.) |
|---|---|---|---|
| 84 | 2.43 | 7.0 | 75.3 |
| 85 | 2.36 | 7.0 | 75.3 |
| 86 | 2.28 | 7.0 | 75.3 |
| 87 | 2.60 | 7.0 | 75.3 |
| 88 | 2.44 | 7.0 | 75.3 |
| 89 | 2.81 | 7.0 | 75.3 |
| 90 | 2.59 | 7.0 | 75.3 |
| 91 | 2.52 | 7.0 | 75.3 |
| 92 | 2.48 | 7.0 | 75.3 |
| 93 | 2.35 | 7.0 | 75.3 |
| 94 | 2.64 | 7.0 | 75.3 |
| 95 | 2.65 | 7.0 | 75.3 |
| 96 | 2.74 | 7.0 | 75.3 |
| 97 | 2.26 | 7.0 | 75.1 |
| 98 | 3.01 | 7.0 | 75.3 |
| 99 | 3.10 | 7.0 | 75.1 |
| 100 | 2.98 | 7.0 | 75.1 |
| 101 | 2.91 | 7.0 | 75.1 |
| 102 | 2.81 | 7.0 | 75.1 |
| 103 | 2.72 | 7.0 | 75.1 |
| 104 | 3.02 | 7.0 | 75.1 |
| 105 | 2.89 | 7.0 | 75.1 |
| 106 | 2.47 | 7.0 | 75.1 |
| 107 | 2.48 | 7.0 | 75.1 |
| 108 | 3.06 | 7.0 | 75.3 |
| 109 | 2.50 | 7.0 | 75.1 |
| 110 | 3.02 | 7.0 | 75.1 |
| 111 | 2.77 | 7.0 | 75.3 |
| 112 | 2.73 | 7.0 | 75.1 |
| 113 | 3.09 | 7.0 | 75.1 |
| 114 | 3.23 | 7.0 | 75.1 |
| 115 | 3.01 | 7.0 | 75.3 |
| 116 | 3.12 | 7.0 | 75.3 |
| 117 | 3.00 | 7.0 | 75.1 |
| 118 | 3.73 | 7.0 | 75.3 |
| 119 | 3.25 | 7.0 | 75.3 |
| 120 | 2.93 | 7.0 | 75.3 |
| 121 | 3.76 | 7.0 | 75.3 |
| 122 | 3.52 | 7.0 | 75.3 |
| 79 | 2.15 | 7.0 | 75.5 |
| 80 | 2.35 | 7.0 | 75.3 |
| 81 | 2.20 | 7.0 | 75.5 |
| 82 | 2.15 | 7.0 | 75.3 |
| 83 | 2.42 | 7.0 | 75.3 |
| 84 | 2.43 | 7.0 | 75.3 |
| 85 | 2.36 | 7.0 | 75.3 |
| 86 | 2.28 | 7.0 | 75.3 |
| 87 | 2.60 | 7.0 | 75.3 |
| 88 | 2.44 | 7.0 | 75.3 |
| 89 | 2.81 | 7.0 | 75.3 |
| 90 | 2.59 | 7.0 | 75.3 |
| 91 | 2.52 | 7.0 | 75.3 |

25 ppt CMHPG
1.0 gpt Zr crosslinker
2.5 ppt Enzyme breaker
Neat, no proppant

| Time (min) | Visc (cP) | Shear Rate (1/s) | Temperature (F.) |
|---|---|---|---|
| 1 | 1501 | 40 | 74.4 |
| 2 | 1363 | 40 | 74.4 |
| 3 | 1262 | 40 | 74.4 |
| 4 | 1217 | 40 | 74.4 |
| 5 | 1171 | 40 | 74.4 |
| 6 | 1118 | 40 | 74.4 |
| 7 | 1090 | 40 | 74.4 |
| 8 | 1063 | 40 | 74.4 |
| 9 | 1015 | 40 | 74.4 |
| 10 | 1000 | 40 | 74.4 |
| 11 | 969 | 40 | 74.4 |
| 12 | 944 | 40 | 74.4 |
| 13 | 913 | 40 | 74.4 |
| 14 | 884 | 40 | 74.4 |
| 15 | 862 | 40 | 74.4 |
| 16 | 859 | 40 | 74.4 |
| 17 | 843 | 40 | 74.4 |
| 18 | 824 | 40 | 74.4 |
| 19 | 815 | 40 | 74.4 |
| 20 | 803 | 40 | 74.4 |
| 21 | 793 | 40 | 74.4 |
| 22 | 753 | 40 | 74.4 |
| 23 | 743 | 40 | 74.2 |
| 24 | 737 | 40 | 74.2 |
| 25 | 727 | 40 | 74.2 |
| 26 | 717 | 40 | 74.4 |
| 27 | 710 | 40 | 74.2 |
| 28 | 697 | 40 | 74.4 |
| 29 | 683 | 40 | 74.4 |
| 30 | 680 | 40 | 74.4 |
| 31 | 673 | 40 | 74.4 |
| 32 | 669 | 40 | 74.4 |
| 33 | 663 | 40 | 74.4 |
| 34 | 656 | 40 | 74.4 |
| 35 | 639 | 40 | 74.4 |
| 36 | 625 | 40 | 74.4 |
| 37 | 621 | 40 | 74.4 |
| 38 | 618 | 40 | 74.4 |
| 39 | 615 | 40 | 74.4 |
| 40 | 611 | 40 | 74.4 |
| 41 | 604 | 40 | 74.4 |
| 42 | 601 | 40 | 74.4 |
| 43 | 594 | 40 | 74.4 |
| 44 | 591 | 40 | 74.4 |
| 45 | 584 | 40 | 74.4 |
| 46 | 581 | 40 | 74.4 |
| 47 | 575 | 40 | 74.4 |
| 48 | 572 | 40 | 74.4 |
| 49 | 569 | 40 | 74.4 |
| 50 | 563 | 40 | 74.4 |
| 51 | 560 | 40 | 74.4 |
| 52 | 556 | 40 | 74.4 |
| 53 | 550 | 40 | 74.4 |
| 54 | 547 | 40 | 74.4 |
| 55 | 547 | 40 | 74.4 |
| 56 | 544 | 40 | 74.4 |
| 57 | 538 | 40 | 74.4 |
| 58 | 535 | 40 | 74.4 |
| 59 | 532 | 40 | 74.6 |
| 60 | 529 | 40 | 74.6 |
| 61 | 526 | 40 | 74.4 |
| 62 | 523 | 40 | 74.4 |
| 63 | 520 | 40 | 74.4 |
| 64 | 520 | 40 | 74.4 |
| 65 | 517 | 40 | 74.6 |
| 66 | 514 | 40 | 74.4 |
| 67 | 511 | 40 | 74.6 |
| 68 | 511 | 40 | 74.4 |
| 69 | 508 | 40 | 74.4 |
| 70 | 505 | 40 | 74.4 |
| 71 | 505 | 40 | 74.6 |
| 72 | 501 | 40 | 74.4 |
| 73 | 501 | 40 | 74.6 |
| 74 | 498 | 40 | 74.6 |
| 75 | 495 | 40 | 74.8 |
| 76 | 492 | 40 | 74.6 |
| 77 | 492 | 40 | 74.6 |
| 78 | 489 | 40 | 74.8 |
| 79 | 486 | 40 | 74.6 |
| 80 | 486 | 40 | 74.6 |
| 81 | 486 | 40 | 74.8 |
| 82 | 480 | 40 | 74.6 |
| 83 | 476 | 40 | 74.8 |
| 84 | 473 | 40 | 74.8 |
| 85 | 473 | 40 | 74.6 |
| 86 | 473 | 40 | 74.8 |
| 87 | 473 | 40 | 74.8 |
| 88 | 470 | 40 | 74.8 |
| 89 | 470 | 40 | 74.8 |
| 90 | 466 | 40 | 74.8 |
| 91 | 463 | 40 | 74.8 |
| 92 | 460 | 40 | 74.6 |
| 93 | 460 | 40 | 74.8 |
| 94 | 460 | 40 | 74.8 |
| 95 | 460 | 40 | 74.6 |
| 96 | 456 | 40 | 74.8 |
| 97 | 456 | 40 | 74.8 |
| 98 | 453 | 40 | 74.8 |
| 99 | 453 | 40 | 74.8 |

TABLE 1-continued

| | | | |
|---|---|---|---|
| 100 | 450 | 40 | 74.8 |
| 101 | 450 | 40 | 74.8 |
| 102 | 450 | 40 | 74.6 |
| 103 | 446 | 40 | 74.8 |
| 104 | 446 | 40 | 74.8 |
| 105 | 446 | 40 | 74.8 |
| 106 | 443 | 40 | 74.8 |
| 107 | 443 | 40 | 74.8 |
| 108 | 440 | 40 | 74.8 |
| 109 | 440 | 40 | 74.6 |
| 110 | 440 | 40 | 74.8 |
| 111 | 440 | 40 | 74.8 |
| 112 | 436 | 40 | 74.8 |
| 113 | 436 | 40 | 74.8 |
| 114 | 433 | 40 | 74.6 |
| 115 | 433 | 40 | 74.8 |
| 116 | 430 | 40 | 74.8 |
| 117 | 430 | 40 | 74.8 |
| 118 | 430 | 40 | 74.8 |
| 119 | 430 | 40 | 74.8 |
| 120 | 426 | 40 | 74.8 |
| 121 | 426 | 40 | 74.8 |
| 122 | 423 | 40 | 74.8 |
| 123 | 423 | 40 | 74.8 |
| 124 | 423 | 40 | 74.8 |
| 125 | 423 | 40 | 74.8 |
| 126 | 423 | 40 | 74.8 |
| 127 | 420 | 40 | 74.8 |
| 128 | 420 | 40 | 74.8 |
| 129 | 420 | 40 | 74.8 |
| 130 | 420 | 40 | 74.8 |
| 131 | 416 | 40 | 74.8 |
| 132 | 416 | 40 | 74.8 |
| 133 | 413 | 40 | 74.8 |
| 134 | 413 | 40 | 74.8 |
| 135 | 413 | 40 | 74.8 |

Figure 8:
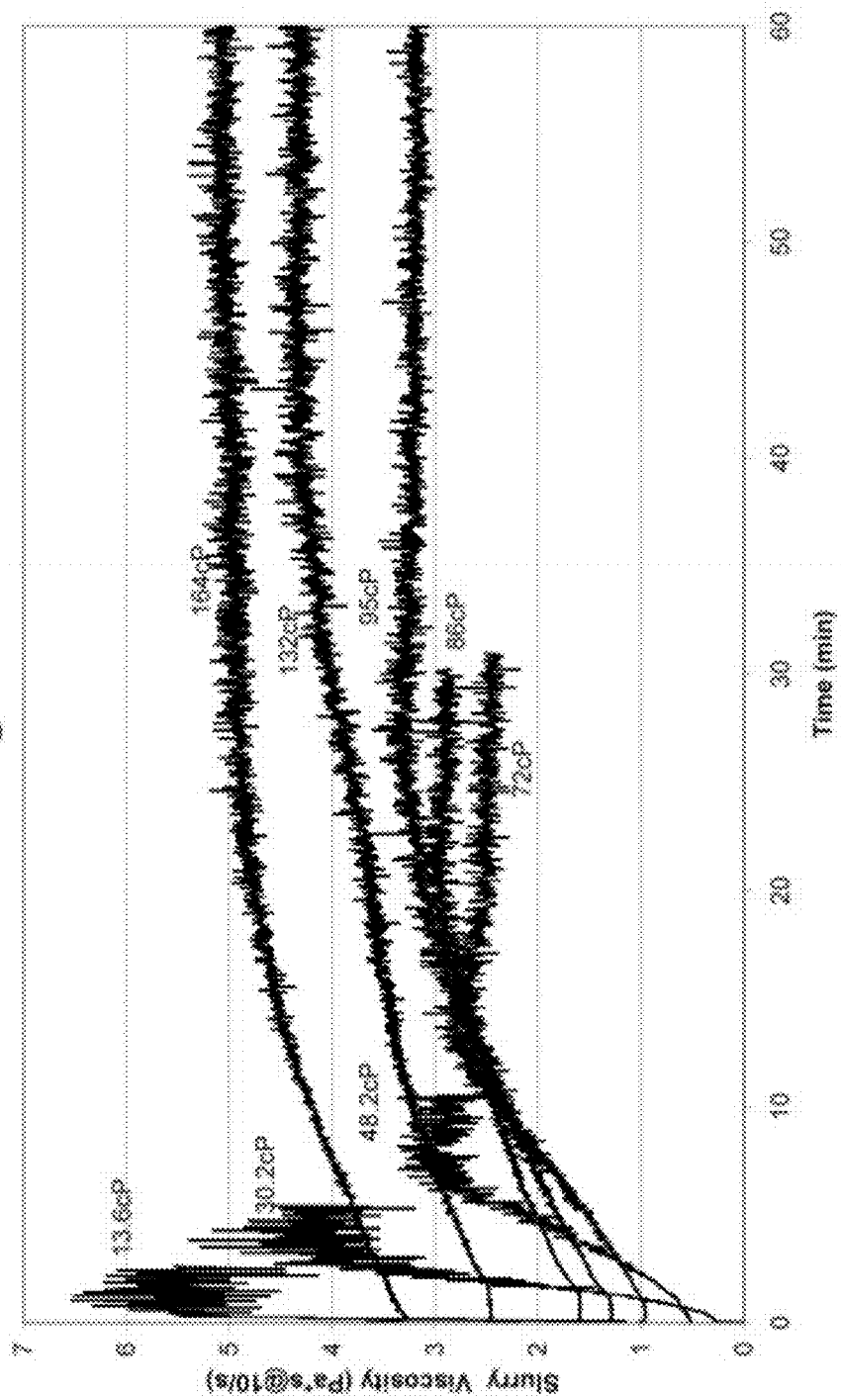
FIG. 8 is a graphical representation of measurements for modified fluids to illustrate a type of comparative analysis that can be made with the particle transport capability measurement depicted in FIG. 7.

In FIG. 8, guar polymers at concentrations of 0.2 to 1.0% were hydrated in water, sand was added to the fluid, and the slurries were measured using the present invention. All of the curves have a positive slope relatively early in the test, indicating that sand settling occurs quickly after the beginning of the test. There is no appreciable time where perfect proppant transport occurs. These curves may be compared to the slopes of the crosslinked gel fluids as an indication of the type of transport and effective gel concentration in the viscous settling region. Data used to make FIG. 8 is shown in Table 2 below.

TABLE 2

18 ppt guar
Vis = 13.6 cP @ 75° F.
8 ppg Econoprop 20/40

| Time (min) | Visc (Pa · s) | Shear Rate (1/s) | Temperature (F.) |
|---|---|---|---|
| 0.18 | 4.17 | 7.0 | 74.1 |
| 0.35 | 5.01 | 7.0 | 74.4 |
| 0.52 | 5.47 | 7.0 | 74.4 |
| 0.68 | 5.51 | 7.0 | 74.4 |
| 0.85 | 5.03 | 7.0 | 74.6 |
| 1.02 | 4.75 | 7.0 | 74.6 |
| 1.18 | 5.18 | 7.0 | 74.8 |
| 1.35 | 5.05 | 7.0 | 74.8 |
| 1.52 | 6.21 | 7.0 | 74.8 |
| 1.68 | 5.39 | 7.0 | 75.0 |
| 1.85 | 5.22 | 7.0 | 75.0 |
| 2.02 | 5.54 | 7.0 | 75.0 |
| 2.18 | 4.14 | 7.0 | 75.0 |
| 2.35 | 5.50 | 7.0 | 75.1 |
| 2.52 | 4.89 | 7.0 | 75.3 |

30 ppt guar
Vis = 30.2 cP @ 75° F.
8 ppg Econoprop 20/40

| Time (min) | Visc (Pa · s) | Shear Rate (1/s) | Temperature (F.) |
|---|---|---|---|
| 0.17 | 0.29 | 7.0 | 73.7 |
| 0.33 | 0.34 | 7.0 | 73.7 |
| 0.50 | 0.42 | 7.0 | 73.7 |
| 0.67 | 0.56 | 7.0 | 73.7 |
| 0.83 | 0.70 | 7.0 | 73.7 |
| 1.00 | 0.87 | 7.0 | 73.7 |
| 1.17 | 1.08 | 7.0 | 73.7 |
| 1.33 | 1.33 | 7.0 | 73.7 |
| 1.50 | 1.69 | 7.0 | 73.7 |
| 1.67 | 1.89 | 7.0 | 73.7 |
| 1.83 | 2.10 | 7.0 | 73.7 |
| 2.00 | 2.36 | 7.0 | 73.7 |
| 2.17 | 2.98 | 7.0 | 73.7 |
| 2.33 | 3.19 | 7.0 | 73.7 |
| 2.50 | 3.92 | 7.0 | 73.9 |
| 2.67 | 4.01 | 7.0 | 73.7 |
| 2.83 | 4.41 | 7.0 | 73.9 |
| 3.00 | 3.10 | 7.0 | 73.7 |
| 3.17 | 4.30 | 7.0 | 73.9 |
| 3.33 | 4.06 | 7.0 | 73.7 |
| 3.50 | 5.27 | 7.0 | 73.7 |
| 3.67 | 4.48 | 7.0 | 73.9 |
| 3.83 | 5.39 | 7.0 | 73.9 |
| 4.00 | 3.95 | 7.0 | 73.9 |
| 4.17 | 3.97 | 7.0 | 73.9 |
| 4.33 | 3.55 | 7.0 | 73.9 |
| 4.50 | 4.40 | 7.0 | 73.9 |
| 4.67 | 4.40 | 7.0 | 73.9 |
| 4.83 | 4.28 | 7.0 | 73.9 |
| 5.00 | 3.88 | 7.0 | 73.9 |
| 5.17 | 4.24 | 7.0 | 73.9 |
| 5.33 | 4.28 | 7.0 | 73.9 |

40 ppt guar
Vis = 48.2 cP @ 75° F.
8 ppg Econoprop 20/40

| Time (min) | Visc (Pa · s) | Shear Rate (1/s) | Temperature (F.) |
|---|---|---|---|
| 0.18 | 0.53 | 7.0 | 74.4 |
| 0.35 | 0.54 | 7.0 | 74.8 |
| 0.52 | 0.58 | 7.0 | 74.8 |
| 0.68 | 0.60 | 7.0 | 74.8 |
| 0.85 | 0.62 | 7.0 | 75.0 |
| 1.02 | 0.64 | 7.0 | 75.0 |
| 1.18 | 0.67 | 7.0 | 75.0 |
| 1.35 | 0.72 | 7.0 | 75.0 |
| 1.52 | 0.77 | 7.0 | 75.0 |
| 1.68 | 0.82 | 7.0 | 75.1 |
| 1.85 | 0.84 | 7.0 | 75.0 |
| 2.02 | 0.93 | 7.0 | 75.0 |
| 2.18 | 0.98 | 7.0 | 75.1 |
| 2.35 | 1.03 | 7.0 | 75.0 |
| 2.52 | 1.10 | 7.0 | 75.1 |
| 2.68 | 1.17 | 7.0 | 75.0 |
| 2.85 | 1.20 | 7.0 | 75.1 |
| 3.02 | 1.27 | 7.0 | 75.1 |
| 3.18 | 1.35 | 7.0 | 75.0 |
| 3.35 | 1.35 | 7.0 | 75.1 |
| 3.52 | 1.43 | 7.0 | 75.1 |
| 3.68 | 1.51 | 7.0 | 75.1 |
| 3.85 | 1.65 | 7.0 | 75.1 |
| 4.02 | 1.68 | 7.0 | 75.1 |
| 4.18 | 1.79 | 7.0 | 75.1 |
| 4.35 | 1.86 | 7.0 | 75.1 |
| 4.52 | 1.91 | 7.0 | 75.3 |
| 4.68 | 2.19 | 7.0 | 75.1 |
| 4.85 | 2.11 | 7.0 | 75.1 |
| 5.02 | 2.33 | 7.0 | 75.1 |
| 5.18 | 2.21 | 7.0 | 75.3 |
| 5.35 | 2.28 | 7.0 | 75.1 |
| 5.52 | 2.35 | 7.0 | 75.3 |

TABLE 2-continued

| Time (min) | Visc (Pa·s) | Shear Rate (1/s) | Temperature (F.) |
|---|---|---|---|
| 5.68 | 2.57 | 7.0 | 75.1 |
| 5.85 | 2.48 | 7.0 | 75.1 |
| 6.02 | 2.81 | 7.0 | 75.3 |
| 6.18 | 2.85 | 7.0 | 75.3 |
| 6.35 | 2.97 | 7.0 | 75.3 |
| 6.52 | 2.67 | 7.0 | 75.3 |
| 6.68 | 2.72 | 7.0 | 75.3 |
| 6.85 | 2.88 | 7.0 | 75.3 |
| 7.02 | 2.90 | 7.0 | 75.3 |
| 7.18 | 2.95 | 7.0 | 75.3 |
| 7.35 | 2.85 | 7.0 | 75.3 |
| 7.52 | 2.99 | 7.0 | 75.3 |
| 7.68 | 2.59 | 7.0 | 75.3 |
| 7.85 | 2.85 | 7.0 | 75.3 |
| 8.02 | 2.97 | 7.0 | 75.3 |
| 8.18 | 3.07 | 7.0 | 75.3 |
| 8.35 | 2.80 | 7.0 | 75.3 |
| 8.52 | 2.91 | 7.0 | 75.3 |
| 8.68 | 2.67 | 7.0 | 75.3 |
| 8.85 | 2.71 | 7.0 | 75.3 |
| 9.02 | 2.92 | 7.0 | 75.3 |
| 9.18 | 3.14 | 7.0 | 75.3 |
| 9.35 | 2.67 | 7.0 | 75.3 |
| 9.52 | 2.86 | 7.0 | 75.3 |
| 9.68 | 3.05 | 7.0 | 75.3 |
| 9.85 | 3.02 | 7.0 | 75.3 |
| 10.02 | 2.73 | 7.0 | 75.3 |
| 10.18 | 2.92 | 7.0 | 75.3 |
| 10.35 | 2.78 | 7.0 | 75.3 |

50 ppt guar
Vis = 72 cP @ 74° F.
8 ppg Econoprop 20/40

| Time (min) | Visc (Pa·s) | Shear Rate (1/s) | Temperature (F.) |
|---|---|---|---|
| 0.35 | 0.96 | 7.0 | 75.0 |
| 0.68 | 0.96 | 7.0 | 74.6 |
| 1.02 | 0.98 | 7.0 | 74.8 |
| 1.35 | 1.03 | 7.0 | 74.8 |
| 1.68 | 1.07 | 7.0 | 74.6 |
| 2.02 | 1.10 | 7.0 | 74.8 |
| 2.35 | 1.15 | 7.0 | 74.8 |
| 2.68 | 1.20 | 7.0 | 74.8 |
| 3.02 | 1.21 | 7.0 | 74.8 |
| 3.35 | 1.29 | 7.0 | 74.8 |
| 3.68 | 1.35 | 7.0 | 74.8 |
| 4.02 | 1.37 | 7.0 | 75.0 |
| 4.35 | 1.41 | 7.0 | 75.0 |
| 4.68 | 1.47 | 7.0 | 74.8 |
| 5.02 | 1.48 | 7.0 | 75.0 |
| 5.35 | 1.65 | 7.0 | 75.0 |
| 5.68 | 1.67 | 7.0 | 75.0 |
| 6.02 | 1.64 | 7.0 | 75.0 |
| 6.35 | 1.79 | 7.0 | 75.0 |
| 6.68 | 1.77 | 7.0 | 75.0 |
| 7.02 | 1.81 | 7.0 | 75.1 |
| 7.35 | 1.85 | 7.0 | 75.0 |
| 7.68 | 1.95 | 7.0 | 75.0 |
| 8.02 | 1.98 | 7.0 | 75.1 |
| 8.35 | 2.12 | 7.0 | 75.0 |
| 8.68 | 2.10 | 7.0 | 75.0 |
| 9.02 | 2.20 | 7.0 | 75.1 |
| 9.35 | 2.19 | 7.0 | 75.3 |
| 9.68 | 2.18 | 7.0 | 75.1 |
| 10.02 | 2.39 | 7.0 | 75.1 |
| 10.35 | 2.38 | 7.0 | 75.3 |
| 10.68 | 2.34 | 7.0 | 75.1 |
| 11.02 | 2.53 | 7.0 | 75.1 |
| 11.35 | 2.43 | 7.0 | 75.1 |
| 11.68 | 2.68 | 7.0 | 75.1 |
| 12.02 | 2.60 | 7.0 | 75.1 |
| 12.35 | 2.72 | 7.0 | 75.3 |
| 12.68 | 2.74 | 7.0 | 75.3 |
| 13.02 | 2.85 | 7.0 | 75.3 |
| 13.35 | 2.80 | 7.0 | 75.3 |
| 13.68 | 2.79 | 7.0 | 75.3 |
| 14.02 | 2.71 | 7.0 | 75.3 |
| 14.35 | 2.64 | 7.0 | 75.3 |
| 14.68 | 2.67 | 7.0 | 75.3 |
| 15.02 | 2.63 | 7.0 | 75.3 |
| 15.35 | 2.94 | 7.0 | 75.3 |
| 15.68 | 2.69 | 7.0 | 75.3 |
| 16.02 | 2.62 | 7.0 | 75.5 |
| 16.35 | 2.66 | 7.0 | 75.3 |
| 16.68 | 2.45 | 7.0 | 75.3 |
| 17.02 | 2.95 | 7.0 | 75.3 |
| 17.35 | 2.62 | 7.0 | 75.5 |
| 17.68 | 2.59 | 7.0 | 75.5 |
| 18.02 | 2.61 | 7.0 | 75.5 |
| 18.35 | 2.57 | 7.0 | 75.5 |
| 18.68 | 2.57 | 7.0 | 75.7 |
| 19.02 | 2.49 | 7.0 | 75.7 |
| 19.35 | 2.40 | 7.0 | 75.7 |
| 19.68 | 2.48 | 7.0 | 75.7 |
| 20.02 | 2.50 | 7.0 | 75.7 |
| 20.35 | 2.49 | 7.0 | 75.5 |
| 20.68 | 2.50 | 7.0 | 75.7 |
| 21.02 | 2.46 | 7.0 | 75.7 |
| 21.35 | 2.46 | 7.0 | 75.7 |
| 21.68 | 2.64 | 7.0 | 75.7 |
| 22.02 | 2.49 | 7.0 | 75.7 |
| 22.35 | 2.51 | 7.0 | 75.7 |
| 22.68 | 2.52 | 7.0 | 75.7 |
| 23.02 | 2.48 | 7.0 | 75.7 |
| 23.35 | 2.58 | 7.0 | 75.7 |
| 23.68 | 2.49 | 7.0 | 75.7 |
| 24.02 | 2.41 | 7.0 | 75.7 |
| 24.35 | 2.47 | 7.0 | 75.7 |
| 24.68 | 2.66 | 7.0 | 75.7 |
| 25.02 | 2.53 | 7.0 | 75.7 |
| 25.35 | 2.48 | 7.0 | 75.7 |
| 25.68 | 2.38 | 7.0 | 75.7 |
| 26.02 | 2.45 | 7.0 | 75.7 |
| 26.35 | 2.49 | 7.0 | 75.7 |
| 26.68 | 2.52 | 7.0 | 75.7 |
| 27.02 | 2.54 | 7.0 | 75.7 |
| 27.35 | 2.36 | 7.0 | 75.7 |
| 27.68 | 2.45 | 7.0 | 75.7 |
| 28.02 | 2.43 | 7.0 | 75.7 |
| 28.35 | 2.51 | 7.0 | 75.7 |
| 28.68 | 2.42 | 7.0 | 75.7 |
| 29.02 | 2.43 | 7.0 | 75.7 |
| 29.35 | 2.42 | 7.0 | 75.7 |
| 29.68 | 2.49 | 7.0 | 75.9 |
| 30.02 | 2.37 | 7.0 | 75.7 |
| 30.35 | 2.51 | 7.0 | 75.7 |
| 30.68 | 2.40 | 7.0 | 75.7 |

60 ppt guar
Vis = 95 cP @ 74° F.
8 ppg Econoprop 20/40

| Time (min) | Visc (Pa·s) | Shear Rate (1/s) | Temperature (F.) |
|---|---|---|---|
| 1.0 | 1.59 | 7.0 | 73.2 |
| 2.0 | 1.70 | 7.0 | 73.5 |
| 3.0 | 1.84 | 7.0 | 73.5 |
| 4.0 | 1.93 | 7.0 | 73.7 |
| 5.0 | 2.03 | 7.0 | 73.9 |
| 6.0 | 2.11 | 7.0 | 73.7 |
| 7.0 | 2.22 | 7.0 | 73.9 |
| 8.0 | 2.31 | 7.0 | 73.9 |
| 9.0 | 2.36 | 7.0 | 73.9 |
| 10.0 | 2.35 | 7.0 | 74.1 |
| 11.0 | 2.59 | 7.0 | 73.9 |
| 12.0 | 2.58 | 7.0 | 74.1 |
| 13.0 | 2.68 | 7.0 | 74.1 |
| 14.0 | 2.67 | 7.0 | 74.1 |
| 15.0 | 2.75 | 7.0 | 74.1 |
| 16.0 | 2.88 | 7.0 | 74.1 |
| 17.0 | 3.01 | 7.0 | 74.1 |
| 18.0 | 2.90 | 7.0 | 74.1 |
| 19.0 | 3.17 | 7.0 | 74.1 |
| 20.0 | 3.14 | 7.0 | 74.1 |
| 21.0 | 3.15 | 7.0 | 74.1 |
| 22.0 | 3.19 | 7.0 | 74.2 |
| 23.0 | 3.24 | 7.0 | 74.2 |

TABLE 2-continued

| Time | Visc | Shear Rate | Temp |
|------|------|------------|------|
| 24.0 | 3.29 | 7.0 | 74.2 |
| 25.0 | 3.32 | 7.0 | 74.4 |
| 26.0 | 3.33 | 7.0 | 74.4 |
| 27.0 | 3.45 | 7.0 | 74.4 |
| 28.0 | 3.38 | 7.0 | 74.4 |
| 29.0 | 3.45 | 7.0 | 74.4 |
| 30.0 | 3.40 | 7.0 | 74.4 |
| 31.0 | 3.31 | 7.0 | 74.4 |
| 32.0 | 3.26 | 7.0 | 74.4 |
| 33.0 | 3.16 | 7.0 | 74.4 |
| 34.0 | 3.36 | 7.0 | 74.4 |
| 35.0 | 3.23 | 7.0 | 74.4 |
| 36.0 | 3.32 | 7.0 | 74.6 |
| 37.0 | 3.24 | 7.0 | 74.8 |
| 38.0 | 3.17 | 7.0 | 74.6 |
| 39.0 | 3.19 | 7.0 | 74.6 |
| 40.0 | 3.18 | 7.0 | 74.8 |
| 41.0 | 3.30 | 7.0 | 74.8 |
| 42.0 | 3.25 | 7.0 | 74.8 |
| 43.0 | 3.16 | 7.0 | 74.8 |
| 44.0 | 3.21 | 7.0 | 74.8 |
| 45.0 | 3.19 | 7.0 | 74.8 |
| 46.0 | 3.28 | 7.0 | 74.8 |
| 47.0 | 3.16 | 7.0 | 74.8 |
| 48.0 | 3.26 | 7.0 | 74.8 |
| 49.0 | 3.27 | 7.0 | 75.0 |
| 50.0 | 3.17 | 7.0 | 74.8 |
| 51.0 | 3.24 | 7.0 | 75.0 |
| 52.0 | 3.24 | 7.0 | 74.8 |
| 53.0 | 3.25 | 7.0 | 75.0 |
| 54.0 | 3.20 | 7.0 | 75.0 |
| 55.0 | 3.23 | 7.0 | 75.0 |
| 56.0 | 3.16 | 7.0 | 75.1 |
| 57.0 | 3.19 | 7.0 | 75.0 |
| 58.0 | 3.14 | 7.0 | 75.1 |
| 59.0 | 3.24 | 7.0 | 75.0 |
| 60.0 | 3.22 | 7.0 | 75.0 |
| 61.0 | 3.07 | 7.0 | 75.1 |
| 62.0 | 3.17 | 7.0 | 75.0 |
| 63.0 | 3.10 | 7.0 | 75.1 |
| 64.0 | 3.14 | 7.0 | 75.1 |
| 65.0 | 3.16 | 7.0 | 75.1 |
| 66.0 | 3.11 | 7.0 | 75.3 |
| 67.0 | 3.12 | 7.0 | 75.1 |
| 68.0 | 3.15 | 7.0 | 75.3 |
| 69.0 | 3.16 | 7.0 | 75.3 |
| 70.0 | 3.09 | 7.0 | 75.3 |
| 71.0 | 3.20 | 7.0 | 75.3 |
| 72.0 | 3.13 | 7.0 | 75.3 |
| 73.0 | 3.16 | 7.0 | 75.3 |
| 74.0 | 3.25 | 7.0 | 75.5 |
| 75.0 | 3.09 | 7.0 | 75.3 |
| 76.0 | 3.19 | 7.0 | 75.5 |
| 77.0 | 3.07 | 7.0 | 75.5 |
| 78.0 | 3.23 | 7.0 | 75.5 |
| 79.0 | 3.14 | 7.0 | 75.3 |
| 80.0 | 3.12 | 7.0 | 75.3 |
| 81.0 | 3.23 | 7.0 | 75.7 |
| 82.0 | 3.16 | 7.0 | 75.7 |
| 83.0 | 3.15 | 7.0 | 75.5 |
| 84.0 | 3.20 | 7.0 | 75.7 |
| 85.0 | 3.24 | 7.0 | 75.7 |
| 86.0 | 3.13 | 7.0 | 75.7 |
| 87.0 | 3.17 | 7.0 | 75.7 |
| 88.0 | 3.28 | 7.0 | 75.7 |
| 89.0 | 3.21 | 7.0 | 75.7 |
| 90.0 | 3.12 | 7.0 | 75.7 |
| 91.0 | 3.28 | 7.0 | 75.7 |
| 92.0 | 3.11 | 7.0 | 75.7 |
| 93.0 | 3.19 | 7.0 | 75.7 |
| 94.0 | 3.12 | 7.0 | 75.7 |
| 95.0 | 3.09 | 7.0 | 75.7 |
| 96.0 | 3.35 | 7.0 | 75.7 |
| 97.0 | 3.23 | 7.0 | 75.9 |
| 98.0 | 3.18 | 7.0 | 75.7 |
| 99.0 | 3.04 | 7.0 | 75.9 |
| 100.0 | 3.16 | 7.0 | 75.9 |
| 101.0 | 3.09 | 7.0 | 75.7 |
| 102.0 | 3.14 | 7.0 | 75.9 |
| 103.0 | 3.12 | 7.0 | 75.9 |
| 104.0 | 3.04 | 7.0 | 75.9 |
| 105.0 | 3.21 | 7.0 | 75.9 |
| 106.0 | 3.07 | 7.0 | 75.9 |
| 107.0 | 3.10 | 7.0 | 75.9 |

70 ppt guar
Vis = 132 cP @ 76° F.
8 ppg Econoprop 20/40

| Time (min) | Visc (Pa · s) | Shear Rate (1/s) | Temperature (F.) |
|------------|---------------|------------------|------------------|
| 1.0 | 2.46 | 7.0 | 75.3 |
| 2.0 | 2.52 | 7.0 | 75.3 |
| 3.0 | 2.65 | 7.0 | 75.5 |
| 4.0 | 2.74 | 7.0 | 75.5 |
| 5.0 | 2.85 | 7.0 | 75.5 |
| 6.0 | 2.93 | 7.0 | 75.7 |
| 7.0 | 2.98 | 7.0 | 75.7 |
| 8.0 | 3.09 | 7.0 | 75.7 |
| 9.0 | 3.16 | 7.0 | 75.7 |
| 10.0 | 3.21 | 7.0 | 75.7 |
| 11.0 | 3.32 | 7.0 | 75.7 |
| 12.0 | 3.33 | 7.0 | 75.7 |
| 13.0 | 3.43 | 7.0 | 75.9 |
| 14.0 | 3.31 | 7.0 | 75.7 |
| 15.0 | 3.46 | 7.0 | 75.9 |
| 16.0 | 3.56 | 7.0 | 75.9 |
| 17.0 | 3.47 | 7.0 | 75.9 |
| 18.0 | 3.59 | 7.0 | 75.9 |
| 19.0 | 3.64 | 7.0 | 75.9 |
| 20.0 | 3.64 | 7.0 | 75.9 |
| 21.0 | 3.69 | 7.0 | 75.9 |
| 22.0 | 3.68 | 7.0 | 76.0 |
| 23.0 | 3.72 | 7.0 | 76.0 |
| 24.0 | 3.74 | 7.0 | 75.9 |
| 25.0 | 3.82 | 7.0 | 76.0 |
| 26.0 | 3.84 | 7.0 | 76.0 |
| 27.0 | 3.83 | 7.0 | 76.0 |
| 28.0 | 4.02 | 7.0 | 76.0 |
| 29.0 | 3.99 | 7.0 | 76.0 |
| 30.0 | 3.97 | 7.0 | 76.0 |
| 31.0 | 4.07 | 7.0 | 76.2 |
| 32.0 | 4.09 | 7.0 | 76.2 |
| 33.0 | 4.09 | 7.0 | 76.2 |
| 34.0 | 4.05 | 7.0 | 76.2 |
| 35.0 | 4.10 | 7.0 | 76.0 |
| 36.0 | 4.16 | 7.0 | 76.2 |
| 37.0 | 4.33 | 7.0 | 76.2 |
| 38.0 | 4.24 | 7.0 | 76.2 |
| 39.0 | 4.18 | 7.0 | 76.2 |
| 40.0 | 4.19 | 7.0 | 76.2 |
| 41.0 | 4.23 | 7.0 | 76.2 |
| 42.0 | 4.38 | 7.0 | 76.2 |
| 43.0 | 4.28 | 7.0 | 76.2 |
| 44.0 | 4.25 | 7.0 | 76.2 |
| 45.0 | 4.35 | 7.0 | 76.4 |
| 46.0 | 4.28 | 7.0 | 76.2 |
| 47.0 | 4.60 | 7.0 | 76.2 |
| 48.0 | 4.23 | 7.0 | 76.4 |
| 49.0 | 4.38 | 7.0 | 76.4 |
| 50.0 | 4.33 | 7.0 | 76.6 |
| 51.0 | 4.33 | 7.0 | 76.6 |
| 52.0 | 4.19 | 7.0 | 76.6 |
| 53.0 | 4.37 | 7.0 | 76.6 |
| 54.0 | 4.50 | 7.0 | 76.6 |
| 55.0 | 4.23 | 7.0 | 76.6 |
| 56.0 | 4.23 | 7.0 | 76.6 |
| 57.0 | 4.32 | 7.0 | 76.6 |
| 58.0 | 4.42 | 7.0 | 76.6 |
| 59.0 | 4.22 | 7.0 | 76.6 |
| 60.0 | 4.47 | 7.0 | 76.6 |
| 61.0 | 4.19 | 7.0 | 76.6 |
| 62.0 | 4.29 | 7.0 | 76.6 |
| 63.0 | 4.31 | 7.0 | 76.6 |
| 64.0 | 4.21 | 7.0 | 76.6 |
| 65.0 | 4.15 | 7.0 | 76.7 |
| 66.0 | 4.49 | 7.0 | 76.6 |
| 67.0 | 4.30 | 7.0 | 76.7 |

TABLE 2-continued

| | | | |
|---|---|---|---|
| 68.0 | 4.28 | 7.0 | 76.6 |
| 69.0 | 4.20 | 7.0 | 76.6 |

80 ppt guar
Vis = 164 cP @ 76° F.
8 ppg Econoprop 20/40

| Time (min) | Visc (Pa·s) | Shear Rate (1/s) | Temperature (F.) |
|---|---|---|---|
| 1.0 | 3.40 | 7.0 | 75.3 |
| 2.0 | 3.49 | 7.0 | 75.3 |
| 3.0 | 3.59 | 7.0 | 75.3 |
| 4.0 | 3.71 | 7.0 | 75.3 |
| 5.0 | 3.74 | 7.0 | 75.3 |
| 6.0 | 3.87 | 7.0 | 75.3 |
| 7.0 | 3.95 | 7.0 | 75.3 |
| 8.0 | 4.04 | 7.0 | 75.3 |
| 9.0 | 4.09 | 7.0 | 75.3 |
| 10.0 | 4.22 | 7.0 | 75.3 |
| 11.0 | 4.26 | 7.0 | 75.3 |
| 12.0 | 4.34 | 7.0 | 75.3 |
| 13.0 | 4.44 | 7.0 | 75.3 |
| 14.0 | 4.52 | 7.0 | 75.3 |
| 15.0 | 4.53 | 7.0 | 75.3 |
| 16.0 | 4.54 | 7.0 | 75.3 |
| 17.0 | 4.58 | 7.0 | 75.3 |
| 18.0 | 4.58 | 7.0 | 75.3 |
| 19.0 | 4.76 | 7.0 | 75.3 |
| 20.0 | 4.76 | 7.0 | 75.3 |
| 21.0 | 4.70 | 7.0 | 75.3 |
| 22.0 | 4.89 | 7.0 | 75.3 |
| 23.0 | 4.83 | 7.0 | 75.3 |
| 24.0 | 4.79 | 7.0 | 75.3 |
| 25.0 | 4.85 | 7.0 | 75.3 |
| 26.0 | 4.81 | 7.0 | 75.3 |
| 27.0 | 4.88 | 7.0 | 75.3 |
| 28.0 | 4.90 | 7.0 | 75.3 |
| 29.0 | 4.80 | 7.0 | 75.3 |
| 30.0 | 4.97 | 7.0 | 75.5 |
| 31.0 | 4.91 | 7.0 | 75.5 |
| 32.0 | 5.09 | 7.0 | 75.5 |
| 33.0 | 4.91 | 7.0 | 75.5 |
| 34.0 | 4.90 | 7.0 | 75.7 |
| 35.0 | 4.96 | 7.0 | 75.3 |
| 36.0 | 4.94 | 7.0 | 75.7 |
| 37.0 | 5.03 | 7.0 | 75.7 |
| 38.0 | 4.97 | 7.0 | 75.7 |
| 39.0 | 4.97 | 7.0 | 75.7 |
| 40.0 | 4.78 | 7.0 | 75.7 |
| 41.0 | 4.83 | 7.0 | 75.7 |
| 42.0 | 5.18 | 7.0 | 75.7 |
| 43.0 | 5.17 | 7.0 | 75.7 |
| 44.0 | 4.78 | 7.0 | 75.7 |
| 45.0 | 4.91 | 7.0 | 75.9 |
| 46.0 | 5.00 | 7.0 | 75.7 |
| 47.0 | 5.17 | 7.0 | 75.7 |
| 48.0 | 5.04 | 7.0 | 75.7 |
| 49.0 | 5.04 | 7.0 | 75.7 |
| 50.0 | 5.11 | 7.0 | 75.9 |
| 51.0 | 5.30 | 7.0 | 75.7 |
| 52.0 | 5.18 | 7.0 | 75.9 |
| 53.0 | 5.14 | 7.0 | 75.9 |
| 54.0 | 5.12 | 7.0 | 75.9 |
| 55.0 | 5.09 | 7.0 | 75.9 |
| 56.0 | 5.15 | 7.0 | 75.9 |
| 57.0 | 5.04 | 7.0 | 75.9 |
| 58.0 | 4.99 | 7.0 | 75.9 |
| 59.0 | 5.11 | 7.0 | 75.9 |
| 60.0 | 5.02 | 7.0 | 75.9 |
| 61.0 | 5.27 | 7.0 | 75.9 |
| 62.0 | 5.04 | 7.0 | 76.0 |
| 63.0 | 5.00 | 7.0 | 75.9 |
| 64.0 | 4.97 | 7.0 | 75.9 |
| 65.0 | 5.15 | 7.0 | 75.9 |
| 66.0 | 5.04 | 7.0 | 75.9 |
| 67.0 | 5.11 | 7.0 | 75.9 |
| 68.0 | 5.02 | 7.0 | 75.9 |
| 69.0 | 5.11 | 7.0 | 75.9 |
| 70.0 | 5.02 | 7.0 | 75.9 |
| 71.0 | 4.98 | 7.0 | 76.0 |
| 72.0 | 5.13 | 7.0 | 75.9 |
| 73.0 | 5.09 | 7.0 | 75.9 |
| 74.0 | 5.06 | 7.0 | 76.0 |
| 75.0 | 5.12 | 7.0 | 75.9 |
| 76.0 | 5.22 | 7.0 | 76.0 |
| 77.0 | 5.11 | 7.0 | 76.0 |
| 78.0 | 5.23 | 7.0 | 76.2 |
| 79.0 | 5.01 | 7.0 | 76.0 |
| 80.0 | 5.27 | 7.0 | 76.0 |
| 81.0 | 5.01 | 7.0 | 76.0 |
| 82.0 | 5.09 | 7.0 | 76.0 |
| 83.0 | 5.09 | 7.0 | 76.0 |
| 84.0 | 4.99 | 7.0 | 76.2 |
| 85.0 | 4.99 | 7.0 | 76.0 |
| 86.0 | 5.01 | 7.0 | 76.0 |
| 87.0 | 4.98 | 7.0 | 76.2 |
| 88.0 | 4.94 | 7.0 | 76.2 |
| 89.0 | 4.95 | 7.0 | 76.2 |
| 90.0 | 5.11 | 7.0 | 76.2 |
| 91.0 | 5.03 | 7.0 | 76.2 |
| 92.0 | 5.28 | 7.0 | 76.2 |
| 93.0 | 4.99 | 7.0 | 76.2 |
| 94.0 | 4.94 | 7.0 | 76.2 |
| 95.0 | 5.02 | 7.0 | 76.2 |
| 96.0 | 5.08 | 7.0 | 76.2 |
| 97.0 | 5.12 | 7.0 | 76.2 |
| 98.0 | 4.96 | 7.0 | 76.4 |
| 99.0 | 4.98 | 7.0 | 76.2 |
| 100.0 | 4.90 | 7.0 | 76.2 |
| 101.0 | 4.88 | 7.0 | 76.2 |
| 102.0 | 5.15 | 7.0 | 76.2 |
| 103.0 | 5.13 | 7.0 | 76.4 |
| 104.0 | 4.92 | 7.0 | 76.4 |
| 105.0 | 4.93 | 7.0 | 76.6 |
| 106.0 | 4.93 | 7.0 | 76.6 |
| 107.0 | 5.12 | 7.0 | 76.6 |
| 108.0 | 4.98 | 7.0 | 76.6 |
| 109.0 | 4.90 | 7.0 | 76.6 |
| 110.0 | 5.06 | 7.0 | 76.6 |
| 111.0 | 5.04 | 7.0 | 76.6 |
| 112.0 | 4.93 | 7.0 | 76.6 |
| 113.0 | 4.96 | 7.0 | 76.6 |
| 114.0 | 4.89 | 7.0 | 76.6 |
| 115.0 | 4.93 | 7.0 | 76.6 |
| 116.0 | 5.12 | 7.0 | 76.6 |
| 117.0 | 5.04 | 7.0 | 76.6 |

Figure 9:
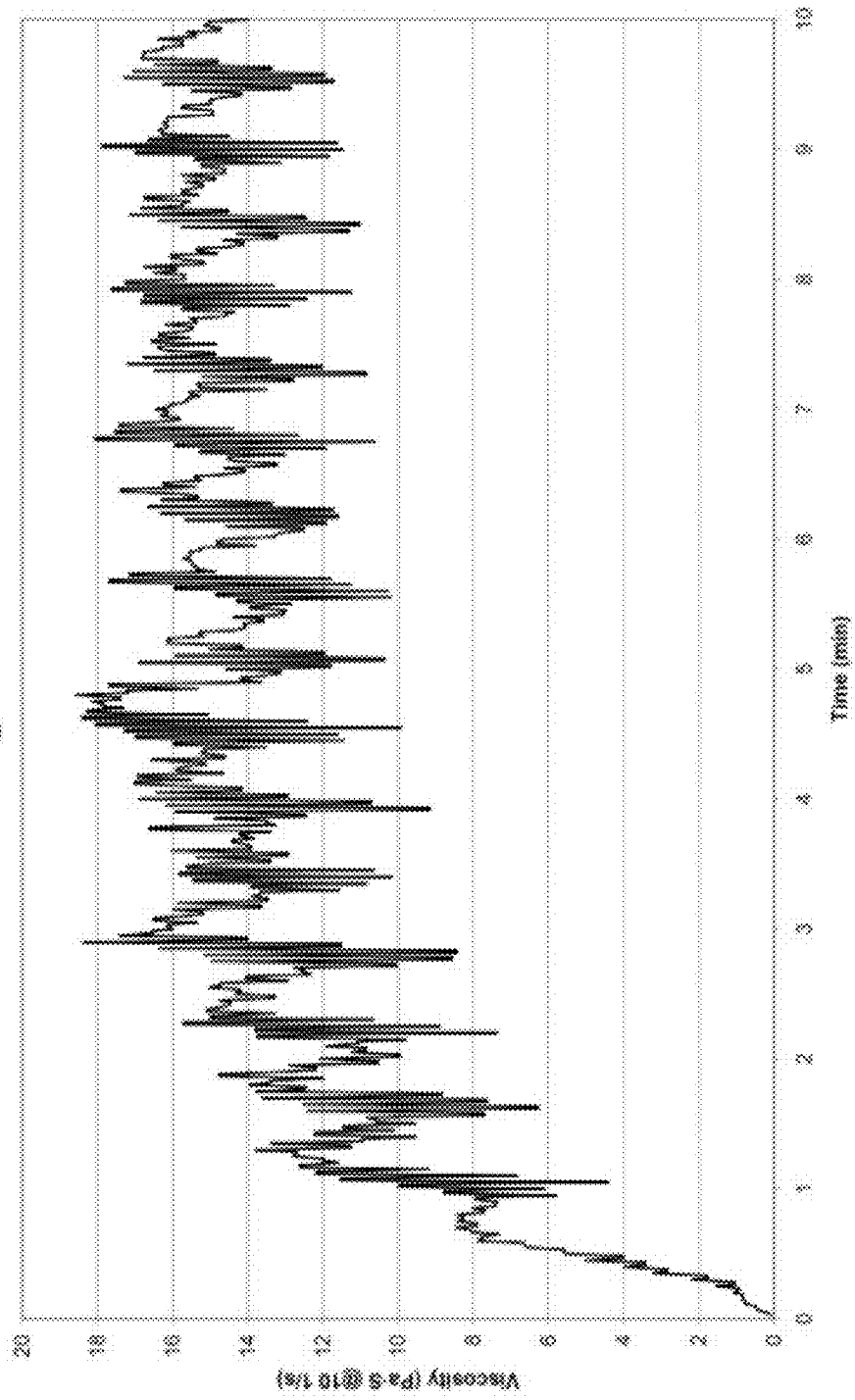
FIG. 9 is a graph showing a response to crosslinking of a test fluid and such fluid becoming viscoelastic.

Referring to FIG. 9, the present invention also may be used to determine crosslink time for the fluid. This typically occurs within a matter of minutes rather than several minutes or hours as in the time periods illustrated in FIG. 7. A graph showing a measurement by the mixer viscometer of the present invention responding to the fluid crosslinking and becoming viscoelastic is shown in FIG. 9. Data used to make FIG. 9 is shown in Table 3 below.

TABLE 3

25 ppt CMHPG
1.0 gpt Zr crosslinker
2.5 ppt Enzyme breaker
Neat, no proppant

| Time (min) | Visc (Pa·s) | Shear Rate (1/s) | Temperature (F.) |
|---|---|---|---|
| 0.18 | 0.83 | 7.0 | 78.5 |
| 0.35 | 3.21 | 7.0 | 77.1 |
| 0.52 | 5.58 | 7.0 | 76.6 |
| 0.68 | 8.06 | 7.0 | 76.2 |
| 0.85 | 8.02 | 7.0 | 76.2 |
| 1.02 | 9.98 | 7.0 | 76.2 |
| 1.18 | 12.60 | 7.0 | 76.2 |
| 1.35 | 13.38 | 7.0 | 76.2 |
| 1.52 | 10.58 | 7.0 | 76.2 |

TABLE 3-continued 25 ppt CMHPG
1.0 gpt Zr crosslinker
2.5 ppt Enzyme breaker
Neat, no proppant

| Time (min) | Visc (Pa·s) | Shear Rate (1/s) | Temperature (F.) |
|---|---|---|---|
| 1.68 | 7.65 | 7.0 | 76.4 |
| 1.85 | 12.00 | 7.0 | 76.2 |
| 2.02 | 9.96 | 7.0 | 76.6 |
| 2.18 | 13.75 | 7.0 | 76.6 |
| 2.35 | 13.27 | 7.0 | 76.6 |
| 2.52 | 14.19 | 7.0 | 76.6 |
| 2.68 | 12.52 | 7.0 | 76.6 |
| 2.85 | 16.33 | 7.0 | 76.6 |
| 3.02 | 16.13 | 7.0 | 76.7 |
| 3.18 | 13.65 | 7.0 | 76.7 |
| 3.35 | 10.83 | 7.0 | 76.6 |
| 3.52 | 13.42 | 7.0 | 76.7 |
| 3.68 | 14.40 | 7.0 | 76.7 |
| 3.85 | 14.85 | 7.0 | 76.7 |
| 4.02 | 12.94 | 7.0 | 76.7 |
| 4.18 | 16.92 | 7.0 | 76.7 |
| 4.35 | 15.25 | 7.0 | 76.7 |
| 4.52 | 17.27 | 7.0 | 76.7 |
| 4.68 | 18.25 | 7.0 | 76.7 |
| 4.85 | 15.35 | 7.0 | 76.7 |
| 5.02 | 11.79 | 7.0 | 76.7 |
| 5.18 | 14.15 | 7.0 | 76.7 |
| 5.35 | 14.10 | 7.0 | 76.9 |
| 5.52 | 14.27 | 7.0 | 76.7 |
| 5.68 | 17.69 | 7.0 | 76.7 |
| 5.85 | 15.71 | 7.0 | 76.7 |
| 6.02 | 13.27 | 7.0 | 76.7 |
| 6.18 | 11.60 | 7.0 | 76.7 |
| 6.35 | 15.88 | 7.0 | 76.7 |
| 6.52 | 14.08 | 7.0 | 76.7 |
| 6.68 | 15.27 | 7.0 | 76.7 |
| 6.85 | 14.40 | 7.0 | 76.7 |
| 7.02 | 16.08 | 7.0 | 76.7 |
| 7.18 | 15.29 | 7.0 | 76.9 |
| 7.35 | 17.19 | 7.0 | 76.7 |
| 7.52 | 16.54 | 7.0 | 76.7 |
| 7.68 | 15.38 | 7.0 | 76.7 |
| 7.85 | 12.44 | 7.0 | 76.7 |
| 8.02 | 15.69 | 7.0 | 76.7 |
| 8.18 | 16.04 | 7.0 | 76.7 |
| 8.35 | 14.27 | 7.0 | 76.7 |
| 8.52 | 14.52 | 7.0 | 76.6 |
| 8.68 | 15.75 | 7.0 | 76.7 |
| 8.85 | 14.63 | 7.0 | 76.7 |
| 9.02 | 17.88 | 7.0 | 76.7 |
| 9.18 | 16.13 | 7.0 | 76.7 |
| 9.35 | 14.96 | 7.0 | 76.7 |
| 9.52 | 11.73 | 7.0 | 76.7 |
| 9.68 | 14.81 | 7.0 | 76.7 |
| 9.85 | 16.38 | 7.0 | 76.6 |
| 10.02 | 14.81 | 7.0 | 76.7 |
| 10.18 | 16.96 | 7.0 | 76.7 |
| 10.35 | 16.69 | 7.0 | 76.7 |
| 10.52 | 15.04 | 7.0 | 76.7 |
| 10.68 | 11.56 | 7.0 | 76.6 |

The method of using the present invention may further include placing in the container at a well site a sample of the fluid taken from a stream of the fluid as the stream is flowing into the well, and performing the steps of the method at the well site as the stream is flowing into the well. Although any suitable embodiment described above may be used in accomplishing this, the open slurry cup embodiment (such as partially illustrated in FIG. 2) is particularly suitable because a sample of fluid can be readily extracted from the stream in known manner, poured into a beaker or other suitable container known in the art, and the beaker or container operatively placed in known manner relative to the open receptacle 10 of the FIG. 2 embodiment. This method enables real-time crosslink time testing at the well site, the results of which can then be used to modify the fluid pumped into the well.

Although the present invention is directed to the determination of particle transport capability, and by which crosslink time can be monitored (such as for real time use at an oil or gas well), other information can be obtained. For example, viscous and elastic properties can be determined by using the torque signal with known mathematical concepts (see, for example, U.S. Pat. No. 5,799,734; J. F. Steffe, Rheological Methods in Food Process Engineering (second edition), Freeman Press, East Lansing, Mich.; and K. L. Mackey, R. G. Morgan and J. F. Steffe, "Effects of Shear-Thinning Behavior on Mixer Viscometry Techniques," Michigan Agricultural Experiment Station Journal Article No. 12280, Apr. 1, 1987; the foregoing incorporated herein by reference).

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. An apparatus for testing a rheological property of a fluid containing particulate, the apparatus comprising:
   a receptacle having a cylindrical sidewall enclosed by a bottom wall defining an axis and a cavity for receiving the fluid containing particulate to be tested;
   at least two inward projections extending inward from the cylindrical sidewall defining a first radial distance from the axis;
   an axial support adapted to be positioned in the cavity of the receptacle, the axial support having at least two outward projections extending outward from the axial support defining a second radial distance from the axis, the second radial distance being less than the first radial distance and wherein the outward projections comprise an outer edge of substantially constant distance from the axis;
   wherein relative rotational motion can be imparted to the receptacle and the axial support such that the inward projections and outward projections can impart a stirring force in the fluid containing particulate;
   wherein at least one of the receptacle or axial support is capable of generating a measurement signal in response to torque forces created from movement of the fluid containing particulate within the receptacle upon the relative rotational motion between the receptacle and the axial support.

2. The apparatus of claim 1, wherein the relative rotational motion can be imparted by rotational motion of the receptacle and the axial support is capable of generating a measurement signal in response to torque forces created from movement of the fluid containing particulate within the receptacle.

3. The apparatus of claim 1, wherein the inward projections comprise an inner edge of substantially constant distance from the axis.

4. The apparatus of claim 1, further comprising a cage comprising the at least two inward projections, the cage positioned within the receptacle.

5. The apparatus of claim 4, wherein the cage can be inserted and removed from the receptacle.

6. The apparatus of claim 4, wherein the cage can be attached to the receptacle by frictional pressure exerted on the sidewall by the cage.

7. The apparatus of claim 1, wherein the receptacle further comprises a removable end portion forming the bottom wall.

8. The apparatus of claim 1, further comprising at least two secondary inward projections extending inward from the cylindrical sidewall at a location above the at least two inward projections and the at least two outward projections.

9. The apparatus of claim 8, wherein portions of the at least two secondary inward projections extend closer to the axis than the at least two inward projections.

10. The apparatus of claim 8, further comprising a cage comprising the at least two secondary inward projections, the cage positioned within the receptacle.

11. The apparatus of claim 8, wherein the at least two secondary inward projections comprise an inner edge of varying distance from the axis.

12. The apparatus of claim 1, wherein the receptacle and axial support are capable of attachment to a viscometer.

13. The apparatus of claim 1, wherein the receptacle has an interior diameter of between 0.5 to 4.0 inches.

14. An apparatus for testing a rheological property of a fluid containing a particulate, the apparatus comprising:
  a receptacle having a cylindrical sidewall enclosed by a bottom wall defining an axis and a cavity for receiving the fluid containing particulate to be tested, the receptacle having an interior diameter of between 0.5 to 4.0 inches;
  at least two inward projections extending inward from the cylindrical sidewall that comprise an inner edge of substantially constant distance from the axis, defining a first radial distance from the axis, the inward projections extending inward from the cylindrical sidewall from 0.1 to 1.5 inches;
  an axial support adapted to be positioned in the cavity of the receptacle, the axial support having at least two outward projections extending outward from the axial support that comprise an outer edge of substantially constant distance from the axis, defining a second radial distance from the axis, the second radial distance being less than the first radial distance, the outward projections extending outward from the axis from 0.1 to 1.5 inches;
  a removable cage comprising the at least two inward projections positioned within the receptacle attached to the receptacle by frictional pressure exerted on the sidewall by the cage;
  the cage further comprising at least two secondary inward projections extending inward from the cylindrical sidewall at a location above the at least two inward projections and the at least two outward projections, the secondary inward projections comprising an inner edge of varying distance from the axis wherein portions of the secondary inward projections extend closer to the axis than the inward projections;
  wherein the receptacle and axial support are capable of attachment to a viscometer;
  wherein relative rotational motion can be imparted to the receptacle and the axial support by rotational motion of the receptacle such that the inward projections and outward projections can impart a stirring force in the fluid containing particulate;
  wherein the axial support is capable of generating an electrical measurement signal in response to torque forces created from movement of the fluid containing particulate within the receptacle.

15. A method of testing a rheological property of a fluid containing particulate, comprising:
  placing a sample of the fluid containing a particulate in a receptacle having a cylindrical sidewall enclosed by a bottom wall defining an axis, the receptacle having at least two inward projections extending inward from the cylindrical sidewall defining a first radial distance from the axis;
  connecting the receptacle to a viscometer having an axial support from which at least two outward projections extend outward from the axial support defining a second radial distance from the axis, the second radial distance being less than the first radial distance and wherein the outward projections comprise an outer edge of substantially constant distance from the axis;
  creating relative rotational movement between the receptacle and the axial support such that the inward and outward projections impart a stirring force in the fluid containing a particulate;
  generating a measurement signal in response to torque forces created from the relative movement between the receptacle and the axial support; and
  analyzing the measurement signal to determine an onset of particulate settling by detecting an increase in the torque, whereby elastic particulate transport occurs during a period of time before the onset of particulate settling, and viscous settling occurs during a period of time after the onset of particulate settling.

16. The method of claim 15, wherein the measurement signal comprises an electrical signal.

17. The method of claim 15, wherein the increase in the torque is characterized by an upward inflection in a graph of the torque versus time.

18. The method of claim 15, wherein the period of elastic particulate transport occurring near the onset of particulate settling is characterized by a substantially constant torque.

19. The method of claim 15, wherein the relative rotational movement between the receptacle and the axial support is substantially constant for a period of time before the onset of particulate settling.

20. The method of claim 15, wherein substantially all the particulate remains suspended in the fluid during the period of elastic particulate transport, and substantially all the particulate settles out of the fluid during the period of viscous settling.

21. The method of claim 15, further comprising analyzing the measurement signal to determine a crosslinking time for the fluid.

22. The method of claim 15, further comprising:
  increasing pressure in the connected receptacle such that pressure on the fluid containing a particulate in the receptacle is greater than atmospheric pressure; and
  heating the fluid containing a particulate in the receptacle to a temperature greater than ambient temperature.

23. A method of testing a rheological property of a fluid containing particulate, comprising:
  placing a sample of the fluid containing particulate in a receptacle having a cylindrical sidewall enclosed by a bottom wall defining an axis and a cavity for receiving the fluid containing a particulate to be tested, the receptacle having an interior diameter of between 0.5 to 4.0 inches, the receptacle having at least two inward projections extending inward from the cylindrical sidewall, the inward projections having an inner edge of substantially constant distance from the axis, the inner edge defining a first radial distance from the axis, the inward projections extending inward from the cylindrical sidewall from 0.1 to 1.5 inches;

connecting the receptacle to a viscometer having an axial support adapted to be positioned in the cavity of the receptacle, the axial support having at least two outward projections extending outward from the axial support, the outward projections having an outer edge of substantially constant distance from the axis, the outer edge defining a second radial distance from the axis, the second radial distance being less than the first radial distance and ranging from 0.1 to 1.5 inches;

creating relative rotational movement between the receptacle and the axial support by rotational motion of the receptacle such that the inward projections and outward projections can impart a stirring force in the fluid containing particulate;

generating an electrical signal in response to torque forces on the axial support created from movement of the fluid containing particulate within the receptacle and the axial support; and analyzing the measurement signal to determine an onset of particulate settling by detecting an increase in the torque, whereby elastic particulate transport occurs during a period of time before the onset of particulate settling, and viscous settling occurs during a period of time after the onset of particulate settling;

wherein the increase in the torque is characterized by an upward inflection in a graph of the torque versus time;

wherein the period of elastic particulate transport occurring near the onset of particulate settling is characterized by a substantially constant torque;

wherein the relative rotational movement between the receptacle and the axial support is substantially constant for a period of time before the onset of particulate settling.

24. The method of claim 23, wherein the sample of the fluid containing particulate comprises a gelling agent and a crosslinking agent and further comprising the step of analyzing the measurement signal to determine a crosslinking time for the fluid.

25. The method of claim 23, further comprising:
increasing pressure in the connected receptacle such that pressure on the fluid containing a particulate in the receptacle is greater than atmospheric pressure; and
heating the fluid containing a particulate in the receptacle to a temperature greater than ambient temperature.

26. An apparatus for testing a rheological property of a fluid containing particulate, the apparatus comprising:
a receptacle having a cylindrical sidewall enclosed by a bottom wall defining an axis and a cavity for receiving the fluid containing particulate to be tested;
at least two inward projections extending inward from the cylindrical sidewall defining a first radial distance from the axis, wherein the inward projections comprise an inner edge of substantially constant distance from the axis;
an axial support adapted to be positioned in the cavity of the receptacle, the axial support having at least two outward projections extending outward from the axial support defining a second radial distance from the axis, the second radial distance being less than the first radial distance;
wherein relative rotational motion can be imparted to the receptacle and the axial support such that the inward projections and outward projections can impart a stirring force in the fluid containing particulate;
wherein at least one of the receptacle or axial support is capable of generating a measurement signal in response to torque forces created from movement of the fluid containing particulate within the receptacle upon the relative rotational motion between the receptacle and the axial support.

27. The apparatus of claim 26, wherein the outward projections comprise an outer edge of substantially constant distance from the axis.

28. The apparatus of claim 26, further comprising a cage comprising the at least two inward projections, the cage positioned within the receptacle.

29. The apparatus of claim 26, further comprising at least two secondary inward projections extending inward from the cylindrical sidewall at a location above the at least two inward projections and the at least two outward projections.

30. An apparatus for testing a rheological property of a fluid containing particulate, the apparatus comprising:
a receptacle having a cylindrical sidewall enclosed by a bottom wall defining an axis and a cavity for receiving the fluid containing particulate to be tested;
at least two inward projections extending inward from the cylindrical sidewall defining a first radial distance from the axis;
an axial support adapted to be positioned in the cavity of the receptacle, the axial support having at least two outward projections extending outward from the axial support defining a second radial distance from the axis, the second radial distance being less than the first radial distance;
at least two secondary inward projections extending inward from the cylindrical sidewall at a location above the at least two inward projections and the at least two outward projections;
wherein relative rotational motion can be imparted to the receptacle and the axial support such that the inward projections and outward projections can impart a stirring force in the fluid containing particulate;
wherein at least one of the receptacle or axial support is capable of generating a measurement signal in response to torque forces created from movement of the fluid containing particulate within the receptacle upon the relative rotational motion between the receptacle and the axial support.

31. The apparatus of claim 30, wherein portions of the at least two secondary inward projections extend closer to the axis than the at least two inward projections.

32. The apparatus of claim 30, further comprising a cage comprising the at least two secondary inward projections, the cage positioned within the receptacle.

33. The apparatus of claim 30, wherein the at least two secondary inward projections comprise an inner edge of varying distance from the axis.

34. An apparatus for testing a rheological property of a fluid containing particulate, the apparatus comprising:
a receptacle having a cylindrical sidewall enclosed by a bottom wall defining an axis and a cavity for receiving the fluid containing particulate to be tested;
at least two inward projections extending inward from the cylindrical sidewall defining a first radial distance from the axis;

an axial support adapted to be positioned in the cavity of the receptacle, the axial support having at least two outward projections extending outward from the axial support defining a second radial distance from the axis, the second radial distance being less than the first radial distance;

a cage comprising the at least two inward projections, the cage positioned within the receptacle;

wherein relative rotational motion can be imparted to the receptacle and the axial support such that the inward projections and outward projections can impart a stirring force in the fluid containing particulate;

wherein at least one of the receptacle or axial support is capable of generating a measurement signal in response to torque forces created from movement of the fluid containing particulate within the receptacle upon the relative rotational motion between the receptacle and the axial support.

35. The apparatus of claim 34, wherein the cage can be inserted and removed from the receptacle.

36. The apparatus of claim 34, wherein the cage can be attached to the receptacle by frictional pressure exerted on the sidewall by the cage.

37. A method of testing a rheological property of a fluid containing particulate, comprising:

placing a sample of the fluid containing a particulate in a receptacle having a cylindrical sidewall enclosed by a bottom wall defining an axis, the receptacle having at least two inward projections extending inward from the cylindrical sidewall defining a first radial distance from the axis, wherein the inward projections comprise an inner edge of substantially constant distance from the axis;

connecting the receptacle to a viscometer having an axial support from which at least two outward projections extend outward from the axial support defining a second radial distance from the axis, the second radial distance being less than the first radial distance;

creating relative rotational movement between the receptacle and the axial support such that the inward and outward projections impart a stirring force in the fluid containing a particulate;

generating a measurement signal in response to torque forces created from the relative movement between the receptacle and the axial support; and analyzing the measurement signal to determine an onset of particulate settling by detecting an increase in the torque, whereby elastic particulate transport occurs during a period of time before the onset of particulate settling, and viscous settling occurs during a period of time after the onset of particulate settling.

38. The method of claim 37, wherein the period of elastic particulate transport occurring near the onset of particulate settling is characterized by a substantially constant torque.

39. The method of claim 37, wherein the relative rotational movement between the receptacle and the axial support is substantially constant for a period of time before the onset of particulate settling.

40. The method of claim 37, further comprising:

increasing pressure in the connected receptacle such that pressure on the fluid containing a particulate in the receptacle is greater than atmospheric pressure; and heating the fluid containing a particulate in the receptacle to a temperature greater than ambient temperature.

41. A method of testing a rheological property of a fluid containing particulate, comprising:

placing a sample of the fluid containing a particulate in a receptacle having a cylindrical sidewall enclosed by a bottom wall defining an axis, the receptacle having at least two inward projections extending inward from the cylindrical sidewall defining a first radial distance from the axis;

connecting the receptacle to a viscometer having an axial support from which at least two outward projections extend outward from the axial support defining a second radial distance from the axis, the second radial distance being less than the first radial distance;

wherein at least two secondary inward projections extending inward from the cylindrical sidewall at a location above the at least two inward projections and the at least two outward projections;

creating relative rotational movement between the receptacle and the axial support such that the inward and outward projections impart a stirring force in the fluid containing a particulate;

generating a measurement signal in response to torque forces created from the relative movement between the receptacle and the axial support; and analyzing the measurement signal to determine an onset of particulate settling by detecting an increase in the torque, whereby elastic particulate transport occurs during a period of time before the onset of particulate settling, and viscous settling occurs during a period of time after the onset of particulate settling.

42. The apparatus of claim 41, wherein portions of the at least two secondary inward projections extend closer to the axis than the at least two inward projections.

43. The apparatus of claim 41, further comprising a cage comprising the at least two secondary inward projections, the cage positioned within the receptacle.

44. The apparatus of claim 43, wherein the cage can be attached to the receptacle by frictional pressure exerted on the sidewall by the cage.

45. The apparatus of claim 41, wherein the at least two secondary inward projections comprise an inner edge of varying distance from the axis.

46. A method of testing a rheological property of a fluid containing particulate, comprising:

placing a sample of the fluid containing a particulate in a receptacle having a cylindrical sidewall enclosed by a bottom wall defining an axis, the receptacle having at least two inward projections extending inward from the cylindrical sidewall defining a first radial distance from the axis and further comprising a removable cage comprising the at least two inward projections, the cage positioned within the receptacle;

connecting the receptacle to a viscometer having an axial support from which at least two outward projections extend outward from the axial support defining a second radial distance from the axis, the second radial distance being less than the first radial distance;

creating relative rotational movement between the receptacle and the axial support such that the inward and outward projections impart a stirring force in the fluid containing a particulate;

generating a measurement signal in response to torque forces created from the relative movement between the receptacle and the axial support; and analyzing the measurement signal to determine an onset of particulate settling by detecting an increase in the torque, whereby elastic particulate transport occurs during a period of time before the onset of particulate settling, and viscous settling occurs during a period of time after the onset of particulate settling.

* * * * *